United States Patent [19]

Rosenberg

[11] Patent Number: 6,056,952
[45] Date of Patent: May 2, 2000

[54] SELECTIVE ELIMINATION OF T CELLS THAT RECOGNIZE SPECIFIC PRESELECTED TARGETS

[75] Inventor: Amy Sonya Rosenberg, Kensington, Md.

[73] Assignee: The United States of America as represented by the Department of Health and Human Services, Washington, D.C.

[21] Appl. No.: 09/029,045

[22] PCT Filed: Aug. 29, 1996

[86] PCT No.: PCT/US96/13873

§ 371 Date: Jun. 2, 1998

§ 102(e) Date: Jun. 2, 1998

[87] PCT Pub. No.: WO97/08328

PCT Pub. Date: Mar. 6, 1997

Related U.S. Application Data

[60] Provisional application No. 60/002,964, Aug. 30, 1995.

[51] Int. Cl.$^7$ .......................... A61K 48/00; C07H 21/04; C12N 15/63; C12N 15/85
[52] U.S. Cl. ..................................... 424/93.21; 435/320.1; 435/325; 536/23.4; 424/93.2; 514/44
[58] Field of Search .......................... 514/44; 424/93.21; 536/23.4; 435/325, 320.1

[56] References Cited

PUBLICATIONS

Greenstein et al. (Mar. 1997) Nature Biotech., vol. 15, 235–238.
Fuchs et al. (1992) Science, vol. 258, 1156–1159.
Gilbert et al. (Jan. 1994) J. Exp. Med., vol. 179, 249–258.
Lanier, L. L. (Apr. 1997) Immunity, vol. 6, 371–378.
Leibson, P. J. (Jun. 1997) Immunity, vol. 6, 655–661.

*Primary Examiner*—Scott D. Priebe
*Assistant Examiner*—Anne Marie S. Beckerleg
*Attorney, Agent, or Firm*—Townsend and Townsend and Crew LLP

[57] ABSTRACT

This invention provides compositions and methods for the elimination of T cells that recognize specific preselected targets. The methods involve providing killer cells (e.g. natural killer cells or cytotoxic T lymphocytes) having a T cell receptor in which the zeta chain is joined to the antigen target of the T cell population it is desired to eliminate. Recognition of the antigen target activates the killer cell thereby inhibiting or destroying the T cell. Where the antigen target is the extracellular domain of a major histocompatibility complex, the method provides a means of mitigating graft rejection or an autoimmune response.

16 Claims, 2 Drawing Sheets

6,056,952

SELECTIVE ELIMINATION OF T CELLS THAT RECOGNIZE SPECIFIC PRESELECTED TARGETS

CROSS REFERENCE TO RELATED APPLICATIONS

This is a continuation-in-part of U.S. Provisional Patent Application U.S. Ser. No. 60/002,964, filed on Aug. 30, 1995 which is herein incorporated by reference for all purposes.

FIELD OF THE INVENTION

The invention relates to methods and compositions for the elimination of T cells that recognize specific preselected targets. In particular, the invention provides methods and compositions for the treatment of graft rejection and autoimmune diseases. In one embodiment, the invention provides modified killer cells that bear a preselected target molecule (e.g. an MHC molecule) attached to a signal transduction molecule (e.g. the zeta (ζ) chain of the T cell receptor or the low-affinity receptor for IgG, FcγRIII (CD 16)). Recognition of the preselected molecule by a T cell activates the killer cell through the signal transduction molecule and the activated killer cell then kills or inhibits the T cell.

BACKGROUND OF THE INVENTION

Autoimmune diseases are pathological states mediated by an undesired immune response. More than 30 autoimmune diseases are presently known; these include many which have received much public attention, including myasthenia gravis (MG) and multiple sclerosis (MS). Characteristic of these diseases is the attack by the immune system on the tissues of the victim—these tissue antigens being non-immunogenic in non-diseased individuals because of the tolerance of the immune system to "self." In autoimmune diseases, this tolerance apparently is compromised, and the tissue of the afflicted subject is treated as an invader—i.e., the immune system sets about destroying this presumed foreign target.

Similarly in graft rejection the recipient of a graft or organ transplant mounts an immune response against the foreign (non-self) tissue. In this case the response is not a loss of tolerance, but rather a legitimate, although undesired, response directed against a foreign tissue.

A crude approach to treating graft or organ rejection or autoimmune disease is, of course, general immunosuppression. This has the obvious disadvantage of crippling the ability of the subject to respond to infectious organisms or tumors. An only slightly more sophisticated approach relies on the removal of antibodies or immune complexes involving the target tissue. This also has adverse side effects, is difficult to accomplish, and is not particularly effective.

Various approaches have been attempted to interdict the immune response to specific antigens. For example, the autoantigen thyroglobulin has been conjugated to ricin A and the conjugate was shown to suppress specifically the in vitro antibody response of lymphocytes which normally respond to this antigen. It was suggested that such immunotoxins would specifically delete autoantibody-secreting lymphocyte clones (Rennie, et al., *Lancet* (Dec. 10, 1983) 1338–1339).

Diener, et. al., *Science* 231: 148–150 (1986) suggested the construction of compounds which cause antigen-specific suppression of lymphocyte function by conjugating daunomycin to the hapten (in this case, of ovalbumin) using an acid-sensitive spacer. The conjugate caused hapten-specific inhibition of antibody secretion by B lymphocytes in vitro and in vivo. A conjugate of daunomycin (with an acid-sensitive spacer) to a monoclonal antibody-specific to T cells also eliminated the response by T-lymphocytes to concanavalin A.

Steerz et al., *J. Immunol.* 134: 841–846 (1985) utilized radiation as the toxic element in a toxin conjugate. Rats were administered a radioactively labeled, purified receptor from electric fish, prior to injection with cold receptor. Injection with this receptor is a standard procedure to induce experimental autoimmune myasthenia gravis (EAMG). Control rats that received preinjection only either of cold receptor or radiolabeled albumin, prior to administration of receptor to induce the disease develop the symptoms of EAMG; those pretreated with radioactively-labeled receptor showed reduced symptoms. It was surmised that the labeled, and therefore destructive, receptor selectively eliminated immunocompetent cells. Similar work utilizing a ricin/receptor conjugate for pretreatment was reported by Killen, et al., *J. Immunol.* 133: 2549–2553 (1984).

A less specific approach which results in the destruction of T cells in general is treatment with an IL-2/toxin conjugate as reported by Hixson, *Medical Tribune*, (Jan. 28, 1988) 4–5. In a converse, but related, approach Liu el al., *Science* 239: 395–397 (1988), report a method to "link up" cytotoxic T cells with a desired target, regardless of the cytotoxic T cell specificity. In this approach, antibody specific to the universal cytotoxic T-lymphocytes to destroy human melanoma cells when melanocyte-stimulating hormone was the hormone used.

Recent experiments have shown that, under certain circumstances, anergy or nonresponsiveness can be induced in autoreactive lymphocytes (see, Schwartz, *Cell* 1073–1081 (1989)). In vitro experiments suggest that antigen presentation by MHC Class II molecules in the absence of co-stimulatory signals induces a state of proliferative non-responsiveness in syngeneic T cells (Quill et. al., *J Immunol.* 138: 3704–3712 (1987)). These reports, however, provide no clear evidence that induction of anergy in vivo is possible or that autoimmune disease or graft rejection can be effectively treated in this manner.

SUMMARY OF THE INVENTION

This invention provides for a method of selectively inhibiting or killing T cells that recognize a specific preselected target molecule. The invention provides modified killer cells that bear a signal transduction molecule (e.g. the zeta (ζ) chain of a T cell receptor) to which is attached the preselected target molecule (e.g. the extracellular domain of a particular MHC molecule). Recognition of the preselected molecule by a T cell activates the killer cell which then kills or inhibits the T cell. Where the preselected molecule is an extracellular domain of an MHC from a xenograft or an allograf, treatment of the graft recipient with the modified killer T cells delays or inhibits graft rejection. Similarly where the preselected molecule is an MHC that binds the antigenic determinant of the autoimmune disease, treatment of the organism with the modified killer T cells mitigates the autoimmune response directed against that antigenic determinant.

This invention provides both for methods and for compositions for the selective inhibition or destruction of T cells that specifically recognize a preselected target molecule. Thus, in one embodiment, this invention provides a method of inhibiting a T cell that specifically recognizes a preselected target molecule. The method involves contacting the T cell with a killer cell comprising a signal transduction molecule attached to a preselected target molecule that is recognized by the T cell. Suitable killer cells include, but are not limited to CTLs, NK cells, macrophages, or the precursors of these cells (e.g. hematopoietic stem cells). The signal transduction molecule may be chemically conjugated to the target molecule, or the transduction molecule/target molecule chimera may be recombinantly expressed as a fusion protein. Preferred signal transduction molecules include the $\zeta$ chain of a T cell receptor, the $\gamma$ chain of an FC receptor, the $\eta$ chain, the $\epsilon$ chain, and the $\delta$ chain, rFC$\epsilon$R1$\beta$, EBV-LMP2A, BLV gp30, TAMs and ARAMs, with the $\zeta$ chain being most preferred.

The killer cell may be an cell that is cytotoxic to other cells when it is activated. Preferred killer cells include cytotoxic T lymphocytes (CTLs) and natural killer (NK) cells.

Preferred target molecules include the extracellular domains of an MHC molecule, more preferably a human MHC molecule (HELA), or the extracellular domains of an MHC molecule (e.g. HLA) complexed with an antigenic determinant of an autoimmune disease (e.g. human type II collagen, or myelin basic protein MBP) or with other peptides.

In a particularly preferred method, the preselected target molecule is the extracellular domain of an MFC molecule of an allograft or a xenograft transplanted to a recipient and the killer cell is administered to the recipient where it inhibits T cells that recognize the MHC molecule and thereby reduces or eliminates a graft rejection response. Administration may be by administration of the killer cell or by administration of a precursor cell (e.g. hematopoietic stem cell) that gives rise to the killer cell. Any of the above-identified signal transduction molecules are suitable, with the $\zeta$ chain of the T cell receptor being preferred. In a preferred embodiment, the target molecule and the signal transduction molecule are expressed as a fusion protein.

In another particularly preferred method, the preselected target molecule is an MHC molecule that presents an antigenic determinant of an autoimmune disease and the killer cell is administered to an organism exhibiting said autoimmune disease where the killer cell inhibits T cells that recognize the antigenic determinant and reduces or eliminates an autoimmune response. Administration may be by administration of the killer cell or by administration of a precursor cell (e.g. hematopoietic stem cell) that gives rise to the killer cell. Any of the above-identified signal transduction molecules are suitable, with the $\zeta$ chain of the T cell receptor being preferred. In a preferred embodiment, the target molecule and the signal transduction molecule are expressed as a fusion protein. The method may additionally involve loading the MHC component of the chimera with the antigenic determinant. This may be accomplished by expression of the antigenic determinant as a fusion with the MHC/signal transduction chimera, by chemical conjugation of the antigenic determinant with the MHC, or by simple exposure of cells bearing the MHC/signal transduction chimera to the antigenic determinant before administration to an organism.

In another embodiment, this invention provides a method of prolonging the life of a cell of a tissue in a host having a T cell that specifically recognizes the tissue and mediates an immune response directed against said tissue. The method involves administering to the host an amount of a killer cell comprising an MHC molecule attached to a signal transduction molecule sufficient to inhibit the T cells that specifically recognize the tissue. The tissue may be an allograft or a xenograft. Preferred allografts or xenografts include, but are not limited to, (transplant) organs such as heart, kidney, or liver or other tissues such as skin. The MHC molecule is preferably the extracellular domain of an MHC characteristic of the allograft or a xenograft. As indicated above, suitable signal transduction molecules include the zeta ($\zeta$) chain of a T cell receptor, the $\gamma$ chain of an FC receptor, the $\eta$ chain, the $\epsilon$ chain, and the $\delta$ chain, rFC$\epsilon$R1B, EBV-LMP2A, BLV gp30, TAMs and ARAMs. The chimeric MHC/signal transduction molecule may be expressed as a fusion molecule. The administered cells include, but are not limited to CTLs, NK cells, macrophages, the precursors of these cells (e.g. hematopoietic stem cells), or cells transformed to express a cytotoxic activity against other cells when activated.

In still another embodiment, this invention provides a method of improving activation of a T cell by a presenting B cell. The method involves contacting the T cell with a B-cell comprising a signal transduction molecule attached to an extracellular domain of a major histocompatibility complex (MHC) molecule. Any of the above-identified signal transduction molecules are suitable, with the $\zeta$ chain being most preferred. A human MHC molecule (HLA) is preferred. The attachment may be by chemical coupling or fusion with fusion being most preferred. The method may be used to treat organisms exhibiting a tumor or a parasitic infection. Treatment involves administering the above-described B-cells (or precursors of these cells) to the organism in an amount sufficient to ameliorate the tumor or parasitic infection.

In still yet another embodiment this invention provides for nucleic acids encoding an extracellular domain of an MHC molecule fused to a signal transduction molecule. Preferred signal transduction molecules include $\zeta$, $\gamma$, $\eta$, $\delta$, and $\epsilon$, with $\gamma$, $\eta$ and $\epsilon$ being more preferred and $\zeta$ being most preferred. Preferred MHC molecules are human MHC molecules (HLA).

This invention also provides a method of inducing immune tolerance of a preselected target molecule. The method involves providing a cell transfected with a nucleic acid encoding the target molecule operably linked to a T-cell specific promoter and administering that cell to a mammal in which tolerance is to be induced. The cell is preferably a cell that matures or differentiates in the thymus. When the cell matures or differentiates in the thymus, it expresses the target molecule where it mediates deletion or anergy of developing T cells reactive to the target molecule. The cell is preferably a bone marrow cell, more preferably a hematopoietic stem cell. The promoter is preferably a promoter that induces expression of a nucleic acid under its control (operably linked) predominantly (more preferably exclusively) when the cell containing the promoter is in the thymus. Particularly preferred promoters include a CD2 promoter, an lck promoter, a CD3 promoter, and a CD4 promoter, with an lck promoter and a CD4 promoter being most preferred.

Finally, this invention also provides for pharmacological compositions and for kits for the practice of the above described methods. Preferred pharmacological compositions include a pharmacologically acceptable excipient and a cell comprising an extracellular domain of a major histocompatibility complex (RMC) molecule attached to a signal transduction molecule. In a preferred embodiment, the MHC is fused to the signal transduction molecule. The pharmacological composition may include any of the above-identified signal transduction molecules with γ, η and ε being more preferred and ζ being most preferred. Suitable cells include cytotoxic T lymphocytes, natural killer (NK) cells, B cells and precursors of any of these cells (e.g. hematopoietic stem cells).

Kits for the practice of this invention include a container containing any of the cells comprising the above-described pharmacological compositions. The kits may additionally or alternatively include expression cassettes encoding a HLA or MHC/ζ chimera, an HLA or MHC under the control of a T cell promoter (e.g., CD2 promoter, lck promoter, CD4 promoter, etc.), or encoding a ζ chain and a restriction site for the easy insertion of a nucleic acid encoding a particular target. The kit may also include grafts (e.g., tissues or organs) expressing the HLA or MHC encoded by the HLA or MHC/ζ construct found in the kit. In addition, the kit may include such items as means for administering the cells, means for expanding the cells ex vivo, various buffers and reagents for the culture and administration of the cells, and means (e.g., vectors) for transforming cells to express the signal transduction molecule/MHC molecule chimeras described above.

Definitions

As used herein the term "killer cell" refers to a cell that has cytotoxic activity and is thus capable of damaging or killing other cells with which it comes in contact. Killer cells are well known to those of skill in the art and include, but are not limited to natural killer (NK) cells, cytotoxic T lymphocytes (CTLs), activated macrophages, and the like. The term killer cells, as used herein also includes cells that have been altered such that, when activated, they manifest a "killer" phenotype, again characterized by the ability to damage or kill other cells.

A "chimeric molecule" is a molecule comprising two or more molecules that exist separately in their native state are but are joined together to form a single molecule having the desired functionality of all of its constituent molecules.

The terms "preselected target molecule" or "preselected target polypeptide" refer to molecules that are recognized by the T cell it is desired to inhibit or destroy. "Preselection" refers to the fact that the identity of the target molecule is selected or known prior to the construction and/or use of cells bearing the target molecule-signal transduction molecule chimera. Preferred preselected target molecules are polypeptides.

The terms "MHC polypeptide", "MHC molecule" or "molecule of the MHC complex", as used herein, refer to a single chain or double chain MHC protein (e.g., the α or β chain of Class II molecules or the heavy chain of Class I molecules) which may constitute all or part of the extracellular portion of the MHC complex (i.e., that portion of the MHC that is accessible to a T cell) which is in other than its native state, for example, not associated with the cell membrane of a cell that normally expresses that MHC.

The "extracellular domain" of class I MHC molecules involves the alpha one, two and three domains, while the extracellular domain of class II MHC molecules involves the alpha one and two domains of the alpha chain and the beta one and two domains of the beta chain. As used herein the "extracellular domain" of an MHC refers both to the native extracellular domains describe above as well as to modified or chemically synthesized extracellular domains. Modified extracellular domains include, but are not limited to MHC domains in which conservative substitutions are made for various amino acids, side chains of various amino acids are modified (e.g. to improve peptide presentation), or amino acids are added or eliminated (e.g. to provide the minimal molecule necessary for presentation).

The term "specifically recognizes" or "T cells specific for a preselected target molecule" refers to a binding reaction which is determinative of the presence of a particular antigen specific T cell in the presence of a heterogeneous population of T cells and other biologics. Thus, under designated immunoassay conditions, the specified T cells bind to particular pre-selected target molecule (e.g. an allogenic MHC) or to a MHC:target molecule complex and do not bind in a significant amount to other target molecules or to other MHC:peptide complexes present in the sample. T cells specific for a preselected target molecule refers to those T cells in a heterogenous population of T cells which bind to and are selectively activated by a particular predetermined target molecule or to a MHC:target molecule complex.

The phrase "MHC capable of presenting a polypeptide (antigenic determinant)" refers to an MHC molecule that binds to a polypeptide (e.g. where the polypeptide is an antigenic determinant of an autoimmune disease) and presents that polypeptide on a cell surface such that it may be specifically recognized by a T cell or a CTL.

The term "allograft" refers to grafts between genetically different members of the same species. In humans, most organ grafts from one individual to another are allografts unless an identical twin is available as a donor. Because an allograft is genetically dissimilar to the host it is often recognized as foreign by the immune system and is rejected in an allograft reaction. "Xenografts" are grafts between different species such as the graft of a baboon heart to a human.

The phrase "inhibiting a T cell" refers to prevention of activation and proliferation of a T cell or to the actual destruction (killing) of a T cell. It is recognized that a killer cell (e.g. CTL) of the present invention, when recognized by the T cell may not always kill the recognizing T cell. However, even damage to the recognizing T cell may lead to an inability of that T cell to proliferate or otherwise participate in an immune response. Thus, inhibition, as used herein when referring to inhibiting a T cell also includes a reduction or elimination of the ability of a T cell to participate in an immune response. Alternatively, the inhibition can be mediated by induction of a cytokine profile that downregulates the activation and/or function of the T cells. Thus, for example, T cells recognizing $D^d$ γ on Th cells may induce secretion of IL-10 or other down-regulator cytokines which do not eliminate the recognizign cell, but rather downregulate its function.

An "undifferentiated cell" refers to a cell that has not yet acquired the characteristics of the mature cell type. Thus, for example, hematopoletic stem cells are undifferentiated cells.

DETAILED DESCRIPTION

Figure 1:
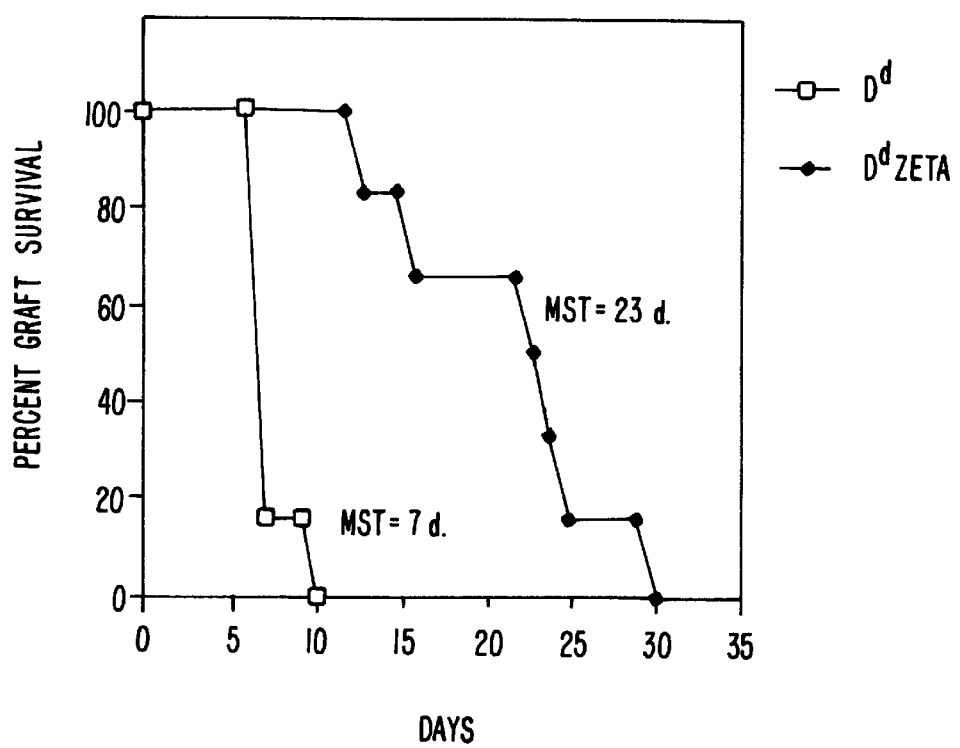
FIG. 1 shows a plot of allograft survival plotted as a function of time for FVB mice infused with lymphocytes expressing either with $D^d$ control (○), or $D^d/ζ$ chimeric (●) molecules. Rejection of $D^d$ skin grafts is delayed in mice infused with lymphocytes expressing $D^d/ζ$, but not those expressing $D^d$ alone. MST=median survival time.

This invention provides methods and compositions for the selective elimination or inhibition of T cells that recognize a specific preselected target molecule. Selective elimination of those T cells capable of recognizing an allograft or xenografi (e.g. where the T cells recognize an MHC molecule characteristic of the allograft or xenograft), will result in the inhibition or elimination of a graft rejection response. Similarly, selective elimination of those T cells capable of recognizing an antigenic determinant of an autoimmune response will result in elimination or mitigation of the autoimmune response.

This invention is premised on the discovery that a killer cell (e.g. a cytotoxic T lymphocyte (CTL) or a natural killer (NK) cell) that is provided with, or that expresses a signal transduction molecule (e.g. a T cell receptor zeta ($\zeta$) chain) having an attached target molecule can be recognized by a T cell specific for that target molecule. The recognition event activates the killer cell which then attacks and inhibits or kills the recognizing T cell thereby depleting the general T cell population of those T cells that recognize the target molecule. As only recognizing T cells are selectively attacked, the killer cells have essentially no effect on other aspects of immune function and do not generally compromise the immune system.

In one embodiment, this invention therefore provides for a killer cell comprising a signal transduction molecule attached to a target molecule. The target molecule may be chemically linked (either directly or through a linker) to the signal transduction molecule, or the target molecule-transduction molecule may be expressed as a fusion protein.

As used herein, a "signal transduction molecule" refers to a molecule that is known to activate various intracellular messenger systems. Such intracellular messenger systems include the activation of one or more tyrosine kinases which ultimately results in the activation of the host cell. Suitable signal transduction molecules include, but are not limited to the zeta ($\zeta$) chain of the T cell receptor (see, e.g. Ashwell and Klausner, *Ann. Rev. Immunol.*, 8: 139–167 (1990), $\eta$, an isoform of $\zeta$, which arises from an alternative splicing pathway (see, e.g., Baniyash et al. *J Biol. Chem.*, 263: 9874–9878 (1988) and Orloffet al. *J. Biol. Chem.*, 264: 114812–14817 (1989)), the $\gamma$ subunit of the Fc$\epsilon$ receptor (see, e.g. Kuster et al., *J. Biol. Chem.*, 265: 6448–6452 (1990)) and the $\delta$ and $\epsilon$ chains of the T cell receptor (see, e.g. Chan et al. *Ann. Rev. Immunol.*, 12: 555–592 (1994)), Ig$\alpha$, Ig$\beta$, rFC$\epsilon$R1$\beta$, EBV-LMP2A, BLV (Bovine leukemia virus) gp30, and such molecules capable of transmitting a signal resulting in cell activation, as a result of interacting with binding proteins. Analysis of the protein sequences in the cytoplasmic domains of signaling molecules has revealed a common motif consisting of two YXXL (SEQ ID NO:13) paired sequences separated by six to eight amino acids. These sequences are known as TAMs (Tyrosine Activation Motifs) or ARAMs (Antigen Recognition Activation Motifs). Any molecule possessing this structure is expected to have suitable signalling capacity for application in this invention.

Suitable target molecules include any molecule that may be recognized by a T cell. This may include glycoproteins, polypeptides, nucleic acids, carbohydrates, and the like. Where the killer cell is used to mitigate a graft rejection response, the target molecule is an extracellular domain from an MHC molecule characteristic of that graft. Conversely, where the killer cell is used to mitigate an autoimmune response, preferred target molecules are autologous MHC molecules capable of presenting an effective domain of the antigenic determinant of the autoimmune disease or an effective domain of a molecule of the self MHC. An effective domain of a target molecule is one which is recognized by the T cell it is desired to inhibit or eliminate. Thus, for example, in the case of graft rejection, an extracellular domain of a graft MHC molecule comprises a domain that is recognized by a T cell which will mediate an immune response against that graft.

While fusions between various signal transduction molecules (eg. the zeta ($\zeta$) chain of the T cell receptor or the $\gamma$ chain of the FC receptor) are known in the prior art, the signal transduction molecule of these fusions is typically joined to a specific binding (targeting) molecule. A binding molecule is selected that specifically recognizes a particular target (e.g. a marker on a tumor cell) thereby bypassing the typical class restriction of the CTL and specifically targeting the cytotoxic activity of the CTL to the tumor. Thus, for example, Eshar et al. *Proc. Natl. Acad. Sci. USA,* 90: 720–724 (1994) and Moritz et al. *Proc. Natl Acad Sci. USA*, describe the fusion of single chain antibodies to the T cell receptor $\zeta$ chain in CTLs. The antibodies act like "specific binding molecules" that specifically direct the CTL to the target tumor. Similarly, Romeo et al. *Cell,* 64: 1037–1046 (1991), disclose fusion of CD4 to the $\zeta$ chain of the T cell receptor in CTLs to specifically direct the CTL to cells expressing HIV gp120. Finally, the U.S. patents by Capon et al. (U.S. Pat. No. 5,359,046) and its corresponding PCT application (WO 9,210,591) disclose $\zeta$ chain fusions to activate cellular signal transduction mechanisms. Again, Capon et al. select fusion moieties that act as "specific binding molecules" (e.g. antibodies, CD4, CD8) directed to specific targets.

In contrast to the prior art described above, in which a "specific bindinig molecule" is fused to the $\zeta$ chain, the present invention utilizes a non-specific polypeptide target molecule (e.g. MHC). The invention relies on the recognition specificity of the T cell (rather than the chimeric molecule) to effect specific destruction of that T cell. The T cell, in effect, brings about its own demise by recognition of a target molecule on the modified killer cell. Repeated recognition events results in the reduction, inhibition, or elimination of T cells that specifically recognize the target molecule. As indicated above, where the target molecule is a domain of an MHC molecule from an allograft or xenografti the selective removal of T cells that recognize the graft MHC molecule will reduce or eliminate a rejection reaction without generally compromising the immune system. Similarly use of target molecules that are antigenic determinants of autoimmune diseases will mitigate the autoimmune response.

In another embodiment, this invention provides for a method of converting cells which are inefficient antigen presenting cells, such as small resting B cells, into cells which are highly efficient antigen presenting cells (APCs). Small resting B cells expressing native MHC molecules present alloantigen poorly to resting T cells because they inefficiently upregulate expression of co-stimulatory molecules essential for T cell activation. However provision of resting B cells with chimeric molecules (e.g. MHC-signal transduction molecule chimeras such as HLA/$\zeta$ fusions) will cause prompt upregulation of critical co-stimulatory molecules such as B-7, when the MHC complex presents a peptide and thereby mediate efficient activation of T helper cells or CTLs. This is of importance in activating the immune system against responses to tumor antigens or parasite antigens.

I. Mitigation of Graft Rejection

As indicated above, graft rejection is mitigated by the use of MHC molecules as target molecules in the killer cells of this invention. MHC molecules were first identified because of their role in rejection of foreign tissue. Graft-rejection reactions result from the direct response or T cells to MHC molecules which function as histocompatibility antigens. Because of the extreme polymorphism of the MHC, most individuals of the same species have a unique set of histocompatibility antigens. Therefore, T cells respond even to allogeneic grafts (alloreactivity), and MHC molecules are considered alloantigens. Generally $CD4^+$ T cells respond to class II alloantigens and $CD8^-$ T cells respond to class I alloantigens.

In the general paradigm, graft rejection is caused principally by a cell-mediated immune response to alloantigens (primarily MHC molecules) expressed on cells of the graft. Both delayed type hypersensitivity and cell-mediated cytotoxicity reactions have been implicated. The process of graft rejection can be divided into two stages: (1) a sensitization phase in which antigen-reactive lymphocytes of the recipient proliferate in response to alloantigens on the graft and (2) an effector stage in which immune destruction of the graft takes place.

During the sensitization phase, $CD4^+$ and $CD8^+$ T cells recognize alloantigens expressed on cells of the foreign graft and proliferate in response. Both major and minor histocompatibility antigens can be recognized. The response to multiple minor-H antigens is very strong, however, the response to individual minor-H antigens is weak. The amplified population of activated T cells (helper T ($T_H$)) cells is thought to play a central role in inducing the various effector mechanisms of allograft or xenograft rejection.

The effector stage of graft rejection is mediated by a variety of effector mechanisms including cell-mediated reactions involving CTL-mediated cytotoxicity and delayed-typed hypersensitivity ($T_{DTH}$ response). Other mechanisms include antibody+complement lysis and antibody-dependent cell-mediated cytotoxicity (ADCC).

In each of the effector mechanisms, cytokines secreted by helper T ($T_{11}$) cells play a central role. Thus, for example IL-2, IFNγ, and TNF-β have been shown to be important mediators of graft rejection. IL-2 promotes T cell proliferation and is necessary for the generation of cytotoxic lymphocytes (CTLs). IFN-γ is central to the delayed-typed hypersensitivity promoting the influx of macrophage into the graft and their subsequent activation into more destructive cells. Finally, TNF-β has direct cytotoxic activity on the cells of a graft.

In view of the central importance of T cell proliferation in graft rejection, one of skill will appreciate that the reduction, inhibition, or elimination of a T cell population capable of recognizing the graft would reduce or eliminate the graft-rejection response. Indeed, it is generally known that nude mice, which lack a thymus and consequently lack functional T cells are incapable of allograft rejection. This invention, by providing a mechanism to specifically target and debilitate the T cell population capable of recognizing any preselected MHC molecule, thus provides a mechanism for inhibiting or eliminating the graft rejection response.

Thus, in one embodiment, this invention provides compositions and methods for the treatment (mitigation) of graft rejection. The compositions comprise killer cells (or killer cell precursors such as hematopoietic stem cells) having a signal transduction molecule attached to the extracellular domain of an MHC molecule that is characteristic of the graft. An MHC molecule characteristic of the graft is an MC molecule or domain of an MHC molecule that a non-autoreactive T cell can recognize. The characteristic MHC molecule thus allows the graft to be distinguished (as non-self) from the host by the immune system.

Any signal transduction molecule that mediates activation of the host cell when the attached target molecule is recognized (bound) is suitable for this invention. Such signal transduction molecules include, but are not limited to, the ζ chain of the T cell receptor, the γ chain of the FC receptor, the η chain, and other signal transduction molecules discussed above.

Suitable killer cells include any cell that, when activated, exhibits cytotoxic activity against other cells. Such cells include cytotoxic T lymphocytes (CTLs), natural killer cells, cells transformed to express cytotoxic or natural killer activity, cells that give rise to derivative cells that express cytotoxic activity when activated (e.g. hematopoietic stem cells), immortalized cell lines that produce cytotoxic cells (e.g. T cell hybridomas), and the like. In a particularly preferred embodiment the cells are derived from the recipient of the graft.

The methods of reducing or eliminating a graft rejection response involve administering the above-described killer, or precursor, cells (bearing the target MHC molecule characteristic of the graft) to the graft recipient. In a preferred embodiment, the killer cells are administered to the recipient prior to the graft. The T cell population capable or recognizing the graft is thus depleted before the any graft is present to even start provoking an immune response.

The cells may be administered according to methods well known to those of skill in the art. Most typically they will be injected intravenously. However, particularly where hematopoietic stem cells are used, the cells may be injected directly into the bone marrow, however, most bone marrow transplants are accomplished by intravenous injection of the hematopoietic stem cells.

The methods of this invention are suitable for the reduction or elimination of a graft rejection response to any transplanted foreign tissue. Thus the methods may be used (either alone or in combination with immunosuppressants) to prevent rejection of transplanted organs such as heart, kidney, liver, etc. In a particularly preferred embodiment, the methods are used in conjunction with skin grafts (e.g. as in the treatment of burn victims) to reduce or prevent skin graft rejection.

One of skill will appreciate that production of killer cells with specific MHC target molecules for each graft is labor-intensive. However, the use of grafts (e.g. xenografts) from inbred strains of donor organisms, or the use of grafts from organisms that have been transgenically altered to express a heterologous MHC allows the provision of multiple grafts with the same characteristic MHC. The killer cells of this invention may be produced having attached to the signal transduction molecule an extracellular domain that is characteristic of the MHC molecules of the inbred or transgenic strains. Thus, both killer cell and graft may be supplied as "standardized" matched sets.

Similarly, in the case of skin grafts, "synthetic" graft materials derived from numerous sources (e.g. shark basement membrane) may be engineered to express predetermined recognition molecules (e.g. MHC). Here the killer cells of this invention may be produced bearing the same predetermined recognition molecule thus providing both the graft material and a "matched" killer cell to prevent rejection of that graft material.

II. Mitigation of Autoimmune Diseases

It is generally believed that autoimmune diseases result as a consequence of the breakdown in regulation (e.g. clonal anergy or clonal suppression) of autoreactive lymphocytes leading to activation of self-reactive clones of T or B cells thereby generating humoral or cell-mediated responses against self-antigens. Autoimmune diseases are generally characterized as organ-specific and specific autoimmune diseases (see, e.g. Table 1). In organ specific autoimmune diseases the immune response is directed to a target antigen unique to a single organ or gland so the manifestation of symptoms are largely limited to that organ. In systemic autoimmune disease, the response is directed toward a broad range of target antigens and involves a number of organs and tissues.

Experimental autoimmune animal models have revealed a central role for the helper T ($T_H$) cell in the development of autoimmunity. In each experimentally induced autoimmune disease, autoimmune T cell clones can be isolated that induce the autoimmune disease in normal animals. Examination of such T cells generally reveals that they bear the $CD4^+$ membrane marker. Moreover, injections of anti-CD4 monoclonal antibody depleted the $CD4^+$ T cell population and abolished autoimmune symptoms in NZB×NZW mice and in mice with EAE (see, e.g. Waldman *Annu, Rev. Immunol.*, 7: 407 (1989)).

Autoimmunity is thus thought to result, at least proximately, from the recognition of an autoantigen, consisting of a self-HLA+peptide complex by auto-reactive T cells. Since $T_H$ cell recognition of an antigen requires a complex of an MHC molecule, peptide antigen and T cell receptor (TCR), the generation of self reactive $T_H$ cells requires that a susceptible individual possess both MHC molecules and T cell receptors capable of binding self-antigens. Conversely, as indicated above, depletion of T cells involved in self recognition will ameliorate the autoimmune response.

Thus, the administration of killer cells having a signal transduction molecule attached to a an MHC molecule presenting the antigenic determinant of the autoimmune disease will reduce the T cell population that recognizes that antigenic determinant and thereby mitigate the autoimmune response. The phrase an "antigenic determinant of autoimmune disease" refers to an antigen against which an autoimmune response is directed. It is recognized that the antigen may not be causal of the autoimmune disease. It is also recognized that the antigen may not be the only antigen against which an autoimmune response is mounted. However, even where an autoimmune response is directed against many antigens, mitigation of the response against one or more selected "antigenic determinants" will, at least in part, mitigate the autoimmune response. Thus, for example a systemic autoimmune disease such as Sjogren's syndrome may be characterized by an immune response directed against salivary gland, liver, kidney, and thyroid. Reduction of the T cell population capable of recognizing the antigenic determinant on thyroid will mitigate the autoimmnune response directed against that organ.

TABLE 1

Autoimmune diseases in humans

| Disease | Self antigen |
|---|---|
| Organ-Specific Autoimmune Diseases | |
| Addison's disease | Adrenal cells |
| Autoimmune hemolytic anemia | RBC membrane proteins |
| Goodpastures syndrome | Renal and lung basement membranes |
| Graves' disease | Thyroid stimulating hormone receptor |
| Hashimoto's thyroiditis | Thyroid proteins |
| Idiopathic thrombocytopenia purpura | Platelet membrane proteins |
| Insulin-dependent diabetes mellitus | Pancreatic beta cells |
| Myasthenia gravis | Acetylcholine receptors |
| Pernicious anemia | Gastric parietal cells |
| poststreptococcal glomerulonephritis | Kidney cells |
| Systemic Autoimmune Diseases | |
| Spontaneous infertility | Sperm |
| Alkylosing spondylitis | Vertebrate |
| Rheumatoid arthritis | Connective tissue, IgG |
| Scleroderma | Nuclei, heart, lungs, gastrointestinal tract, kidney |
| Sjogren's syndrome | salivary gland, liver, kidney, thyroid |
| Systemic lupus erythematosus | DNA, nuclear protein, RBC and platelet membranes |
| Multiple sclerosis | Brain or white matter |

In a preferred embodiment, treatment of an autoimmune disease occurs when T cells recognize an antigenic determinant of the autoimmune disease when it is presented by the killer cells of this invention. Such antigenic determinants are often produced endogenously. Thus administration of killer cells bearing a MHC fused to a signal transduction molecule where the MHC is capable of binding and presenting the endogenously produced antigenic determinant is sufficient to treat the autoimmune disease or to ameliorate at least one component of the disease.

Alternatively, it is possible to provide killer cells having target molecules that are a combination of MHC and antigenic determinant already in association (e.g. expresses as a fusion, subsequently chemically conjugated, or just loaded by exposure of the killer cells to the antigenic determinant just before administration to the organism. Means of providing loaded MJC molecules are well known to those of skill in the art (see, e.g. U.S. Pat. No. 5,284,935 and related patents).

The table provided above indicates a number of autoantigens that are suitable target molecules for the practice of this invention. In addition, a number of other autoantibodies are well known to those of skill in the art (see, e.g. Avrameas, *Immunol. Today*, 12: 154–159 (1991) for a review). Known autoantigens include, but are not limited to Iodine (anti-I antibodies cause autoimmune hemolytic anemia), nerve glycoprotein (antinerve glycoprotein antibodies incite peripheral neuropathy, type II collagen (induces "collagen arthritis"), *Mycobacterium tuberculosis* coat (induces adjuvant arthritis), glutamic acid decarboxylase (Diabetes mellitus), myelin basic protein (MBP) (appears to be the antigenic determinant for multiple sclerosis), double-stranded DNA, acetylcholine receptor, ribonucleoproteins, histones, phospholipoprotein (PLP), and the like.

Thus, in one embodiment, this invention provides compositions and methods for the treatment (mitigation or amelioration) of an autoimmune response (autoimmune disease). The compositions comprise killer cells (or killer cell precursors) having a signal transduction molecule attached to self MHC and the antigenic determinant of the particular autoimmune response it is desired to treat. Recognition of the antigenic determinant by autoreactive T cells capable of recognizing that determinant results in the death or inhibition of those autoreactive T cells thereby ameliorating the autoimmune response directed against that antigenic determinant.

Any signal transduction molecule that mediates activation of the host cell when the attached target molecule is recognized (bound) is suitable for this invention. Such signal transduction molecules include, but are not limited to, the ζ chain of the T cell receptor, the γ chain of the FC receptor, the η chain, and other signal transduction molecules discussed above.

Suitable killer cells include any cell that, when activated, exhibits cytotoxic activity against other cells. Such cells include cytotoxic T lymphocytes (CTLs), natural killer cells, cells transformed to express cytotoxic or natural killer activity, cells that give rise to derivative cells that express cytotoxic activity when activated (e.g. hematopoietic stem cells), immortalized cell lines that produce cytotoxic cells (e.g. T cell hybridomas), and the like. In a particularly preferred embodiment the cells are derived from the patient expressing the autoimmune response.

The methods of reducing or eliminating an autoimmune response involve administering the above-described killer, or precursor, cells (bearing the target antigenic determinant) to the patient undergoing an autoimmune response.

The cells may be administered according to methods well known to those of skill in the art. Most typically they will be injected intravenously. However, particularly where hematopoietic stem cells are used, the cells may be injected directly into the bone marrow.

III. Improvement of B-Cell Presentation

In another embodiment, this invention provides methods and compositions for the improvement of B-cell presentation of an antigen. Improved presentation, as used herein, refers to an increased likelihood that the presenting B cell will activate the T cell to which it is presenting an antigen.

It is generally known that small resting B cells are relatively inefficient antigen presenting cells and presentation by such cells often does not result in activation of the recognizing T cell (see, e.g. Jenkins et al. *J Immunol.*, 144: 1585–1590 (1990)). It is believed that the inefficient activation is due to the low expression of co-stimulatory molecules (e.g B-7) essential for T cell activation (Id.).

Provision of resting B cells with chimeric molecules (e.g. MHC-signal transduction molecule chimeras such as HLA/ζ fusions) will cause prompt upregulation of critical co-stimulatory molecules such as B-7, when the MHC complex presents a peptide and thereby mediate efficient activation of T helper cells or CTLs. This is of importance in activating the immune system against responses to tumor antigens or parasite antigens.

Thus, in one embodiment, this invention provides for B cells or B cell precursors (e.g. hematopoietic stem cells) comprising an MHC (e.g. an HLA) fused to a signal transduction molecule. Suitable MHC and signal transduction molecules are described above. The B cells are administered to the recipient in the same manner as the killer cells described above.

IV. Preparation of Cells Containing Target-Signal Transduction Molecule Chimeras As indicated above, the present invention relies on the activation of cells bearing target molecule-signal transduction chimeric molecules. The chimeric molecules are preferably membrane bound with the target molecule located extracellularly where it may be recognized by a T cell. Virtually any cell may be modified to bear such a chimeric molecules. However, lymphocytes or lymphocyte precursor cells, in particular cytotoxic lymphocytes (lymphocytes that, when activated, are cytotoxic to other cells), or cytotoxic lymphocyte precursors are most preferred. Thus, particularly preferred cells include cytotoxic T lymphocytes (CTLs), natural killer (NK) cells, hematopoietic stem cells, T cell hybridomas, activated macrophages, monocytes (resting macrophages) and the like. One of skill will appreciate that cells which do not normally express a cytotoxic phenotype when activated, but which have been transformed to express such a phenotype are also suitable. In addition, where it is desired to produce B cells having improved antigen presentation characteristics, B cells and B cell precursors may also be used.

Such cells are well known to those of skill in the art and are available from numerous commercial suppliers, repositories such as the American Type Tissue Collection (ATCC) or may be cultured de novo from appropriate source material according to methods well known to those of skill in the art (see, e.g. *Culture of Animal Cells: A Mammal of Basic Technique*, Freshney, ed. John Wiley & Sons, Inc. N.Y. (1994)).

In a preferred embodiment, the chimeric target molecule/signal transduction molecule includes a transmembrane domain that spans the cell membrane. The chimeric molecule may be designed to include the transmembrane region of the signal transduction molecule joined to the extracellular domain of target molecule (e.g. MHC) or, where the target molecule has a transmembrane region, the chimeric molecule may include the transmembrane region of the target molecule attached to the intracellular domain of the signal transduction molecule. Alternatively, the chimeric molecule may include transmembrane regions from both molecules.

Thus, for example, in the case of MHC/ζ chimeric molecules, the transmembrane domain could originate from either the ζ molecule or from the MHC molecule. The use of the ζ transmembrane region, which contains regions capable of forming disulfide linkages, allows dimerization (or oligomerization or other associations) of the chimeric molecule with other chimeric molecules or with normal cellular signaling molecules (e.g., components of the T cell receptor CD3 complex) whereas the MHC transmembrane region, lacking regions that form disulfide linkages, would not offer such a possibility and therefore tends to limit the orientation of the molecule at the cell surface.

As dimerization, or oligomerization, of signaling molecules has been shown to more efficiently activate cellular function, it is expected that ζ chimeras capable of dimerization or oligomerization will activate cellular function more efficiently and suppress graft rejection more potently than ζ chimeras that do not form dimers or oligomers. Thus, in a particularly preferred embodiment, the ζ chimeric molecules of this invention include, at least a portion of the ζ transmembrane domain. The construction of ζ chimeras containing a MHC transmembrane domain and ζ chimeras containing a ζ transmembrane domain is illustrated in Example 1.

In a preferred embodiment, the target molecule-signal transduction molecule chimeras are prepared as recombinantly expressed fusion proteins. Typically this involves providing a nucleic acid (preferably a deoxyribonucleic acid) that encodes both the target molecule and the signal transduction molecule. The nucleic acid is constructed so that both the sequences encoding the target molecule and the signal transduction molecule are oriented in a common reading frame.

The nucleic acid sequence encoding the chimeric molecule is typically ligated or otherwise constructed into a vector containing appropriate nucleic acids sequences to control the expression of the chimera. The nucleic acid encoding the chimera will be operably linked to appropriate expression control sequences for the host cell. The control sequences will include a promoter and preferably an enhancer derived from immunoglobulin genes, SV40, cytomegalovirus, etc., and a polyadenylation sequence, and may include splice donor and acceptor sequences. The vectors can be transferred into the chosen host cell by well-known methods such as calcium phosphate treatment or electroporation.

Specific means of producing and expressing fusions with signal transduction molecules (e.g. the TCR ζ chain, the Fc receptor γ chain, and the η, 67, or ε chains, rFCεR1β, EBV-LMP2A, BLV gp30, TAMs and ARAMS, etc.) in various "killer" and stem cells are well known to those of skill in the art (see, e.g. Moritz et al, *Proc. Natl. Acad. Sci. USA,* 91: 4318–4322 (1994) who describe the synthesis of anti-ERBB2-scFV/ζ fusion proteins, Romeo et al. *Cell.* 64: 1037–1046 (1991) who describe chimeras between CD4 and ζ, γ, and η; Eshar et al., *Proc. Natl. Acad. Sci. USA,* 90: 720–724 (1993) who describe anti-TNF scFV/γ and anti-TNF scFV/ζ chimeras; Capon et al. U.S. Pat. No. 5,359,046 which describes CD4, CD8, IgG and scAb zeta chain chimeras as well as CD4 and CD8 δ and ε chain chimerics; Howard et al., *J. Exp. Med.,* 176: 139–145 (1992) who describe CD8α/CD3ζ chimeras; Letourneur et al., *Proc. Natl. Acad. Sci. USA,* 88: 8905–8909 (1991) who describe α chain IL-2/ζ and γ chimeras; and Weiss et al., *Cold Springs Harbor Symposium on Quantitative Biology* (1992) who teach the production of CD8/ζ chimeras).

A) Signal Transduction Molecules

As is evident from the references cited above, the nucleic acid sequences encoding numerous signal transduction molecules (e.g., the TCR ζ chain, the Fc receptor γ chain, and the η, δ, or η chains, rFCεR1β, EBV-LMP2A, BLV gp30, TAMs and ARAMs) are well known to those of skill in the art. The methods provided in the cited papers are easily modified to provide signal transduction molecules fused to the target molecules of this invention. This involves providing nucleic acids encoding signal transduction molecules with appropriate restriction sites permitting ligation with a nucleic acid encoding the desired target molecule.

In fact, the cited references teach how to produce the nucleic acids encoding the various signal transduction molecules with appropriate restrictions sites to facilitate the production of chimeric molecules. For example, the constructs including the nucleic acid sequence (cDNA) encoding the murine T cell receptor zeta chain are provided by Weissman et al. *Science,* 239: 1018–1020 (1988). Similarly, a construct containing the human T cell receptor zeta chain cDNA sequence is also provided by Weissman et al. *Proc. Natl Acad. Sci. USA,* 85: 9709–9713 (1988)). While signal transduction molecules from any vertebrate are suitable for this invention, in a preferred embodiment the signal transduction molecules are derived from a mammal and more preferably are selected to match the species from which the killer cells are derived. Thus where human killer cells are used, a human signal transduction molecule is preferred.

Using the known sequence information for the signal transduction molecules indicated in the various references described above, the DNA encoding these respective chains may be chemically synthesized de novo, or isolated and amplified from total genomic DNA or from cDNA libraries. Chemical synthesis may be by generally known methods such as the phosphotriester method of Narang et al. *Meth. Enzymol.* 68: 90–99 (1979); the phosphodiester method of Brown et al., *Meth. Enzymol* 68: 109–151 (1979); the diethylphosphoramidite method of Beaucage et al., *Tetra. Lett.,* 22: 1859–1862 (198 1); and the solid support method of U.S. Pat. No. 4,458,066, all incorporated by reference herein.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the DNA encoding a signal transduction molecule is amplified from a cDNA library. Methods for amplifying and isolating known nucleic acid sequences are routine to those of skill in the art. Thus, for example, Eshar et al. *Proc. Natl. Acad. Sci. USA.,* 90: 720–724 (1994), provides primers for PCR amplification of the γ chain from a human cDNA clone (Kuster et al. *J. Biol. Chem.,* 265: 6488–6452 (1990)) or the ζ chain from Jurkat cDNA (see FIG. 1). The primers are selected to introduce BstEII and Xho I restriction sites at the 5' and 3' ends respectively to facilitate cloning.

Primers and methods of amplification of the ζ, γ, δ, and epsilon chains ε chains are also provided in U.S. Pat. No. 5,359,046. PCR cloning of the γ and ζ chains is described by Higuchi et al. *Nucleic Acids Res.* 16: 7351–7367 (1988). PCR cloning of the CD8ζ chain is described by Irving and Weiss, *Cell,* 64: 891 (1991). Clones of the wildtype CD25/ζ and mutated CD25/ζYF cDNAs in the pHβAPr-1-neo expression vector are also available (see Wegner et al. *Cell,* 68: 83–95 (1992)). In addition, methods of amplifying the ζ chain from the Weissman et al. CD3ζ construct (clone pGEM3zζ) are provided by Howard et al. *J Exp. Med.,* 176: 139–145 (1992). Similarly, methods of amplifying the murine the murine ζ chain, creating a chimeric molecule and expressing that molecule in a lymphocyte are provided in Example 1.

B) Target Molecules

Means of obtaining DNAs encoding MECs or antigenic determinants of autoimmune diseases are well known to those of skill in the art. For example, the MHC is extremely well characterized (see, e.g. *Fundamental Immunology,* Paul, ed., Raven Press, N.Y. (1993)) and nucleic acid sequences of numerous MHC molecules are well known to those of skill in the art. Moreover, where the MHC is selected to correspond to the MHC from a graft, the nucleic acid encoding that MHC may be determined using routine methods well known to those of skill in the art.

1) Cloning of MHC genes

One such method that can be used is to purify the desired MHC polypeptide, obtain a partial amino acid sequence, synthesize a nucleotide probe based on the amino acid sequence, and use the probe to identify clones that harbor the desired gene from a cDNA or genomic library.

MHC polypeptides can be easily obtained by isolation from lymphocytes from the individual providing the graft, from the individual expressing an MHC antigenic determinant of an autoimmune disease, or from the individual whose B cells are to be modified. The MHC molecules, for example, may be isolated from human B cells immortalized by transformation with a replication deficient Epstein-Barr virus, utilizing techniques known in the art.

MHC polypeptides have been isolated from a multiplicity of cells using a variety of techniques including solubilization by treatment with papain, by treatment with 3M KCl, and by treatment with detergent. In a preferred method detergent extraction of Class II protein from lymphocytes followed by affinity purification is used. Detergent can then be removed by selected methods such as dialysis. Other purification methods for MHC polypeptides are well known to those of skill in the art. For example, methods for purifying the murine I-A (Class II) histocompatibility proteins have been disclosed by Turkewitz et al., *Molecular Immunology* 20: 1139–1147 (1983). These methods, which are also suitable for class I molecules, involve preparation of a soluble membrane extract from cells containing the desired MHC molecule using nonionic detergents, such as NP-40. Tween 80 and the like. The MHC molecules are then purified by affinity chromatography, using a column containing antibodies raised against the desired MHC molecule. Use of 0.02% Tween-80 in the elution buffer is helpful to eliminate aggregation of the purified molecules. Isolation of human HLA antigens has been described by Springer et al., *Proc. Natl. Acad. Sci. USA* 73: 2481–2485 1976); Clementson et al., in *Membrane Proteins*, Azzi. A., ed; and by Bjorkman, P., Ph.D. Thesis Harvard (1984). Soluble HLA-A2 can be purified after papain digestion of plasma membranes from the homozygous human lymphoblastoid cell line J-Y as described by Turner et al., *J. Biol. Chem.* 252: 7555–7567 (1977). Papain cleaves the 44 kd chain close to the transmembrane region yielding a molecule comprised of alpha$_1$, alpha$_2$, alpha$_3$, and β$_2$ microglobulin. Cloning of the Class II genes (as described by Estees et al., pp 3–19 in *Regulation of Immune Gene Expression*, Feldman et al., eds. Humana Press (I 985)) permits manipulation of the Class II MHC binding domains.

After isolation of the MHC molecule, a partial amino acid sequence is determined and degenerate oligonucleotide probes, designed to hybridize to the desired gene, are synthesized. Amino acid sequencing is performed and oligonucleotide probes are synthesized according to standard techniques as described, for instance, in Sambrook et al., *Molecular Cloning: A Laboratory Manual (*2nd ed.), Vols. 1–3, Cold Spring Harbor Laboratory (1989).

Genomic or cDNA libraries are prepared according to standard techniques as described, for instance, in Sambrook et al., supra. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and cosmids.

To prepare cDNA, MRNA from the organism of interest is first isolated. Eukaryotic MnRNA has at its 3' end a string of adenine nucleotide residues known as the poly-A tail. Short chains of oligo d-T nucleotides are then hybridized with the poly-A tails serving as a primer for the enzyme reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or λ phage vector for propagation in *E. coli*.

Identification of clones in either genomic or cDNA libraries harboring the desired nucleic acid segments is performed by either nucleic acid hybridization, or immunological detection of the encoded protein if an expression vector is used. The bacterial colonies are then replica plated on solid support, such as nitrocellulose filters. The cells are lysed and probed with either oligonucleotide probes described above or with antibodies to the desired protein.

Other methods well known to those skilled in the art can also be used to identify desired genes. For example, amplification techniques, such as the polymerase chain reaction (PCR) can be used to amplify the desired nucleotide sequence. U.S. Pat. Nos. 4,683,195 and 4,683,202 describe this method. Sequences amplified by PCR can be purified from agarose gels and cloned into an appropriate vector according to standard techniques.

In situations where the graft is derived from an inbred strain (most typically where the graft is a xenograft), the nucleic acid encoding an MHC molecule may already be known. This is particularly true where the xenograft is derived from an organism has been transformed to express a heterologous MHC (e.g. porcine recombinantly modified to express human MHC).

Finally, numerous MHC sequences are known and available through commercial sources and various repositories such as the American Type Tissue Culture Collection (ATCC).

2) Cloning of Antigenic Determinants of Autoimmune Diseases

As indicated above, in some embodiments, rather than relying on endogenous antigenic determinants presented by the MHC/signal transduction molecule chimeras of this invention, the antigenic determinant (e.g. polypeptide) may be administered in combination with the chimera-bearing cells of this invention. The antigenic determinants may be expressed in fusion with the MHC component of the chimeric molecule, chemically coupled to the chimeric molecule (e.g. direct covalent bonding through reactive sites on both molecules or through a linker) or bound to the MHC component through ionic, hydrophobic, and electrostatic interactions (e.g. normal MHC binding). Means of providing MHC complexes "loaded" with a particular peptide are well known to those of skill in the art (see, e.g. U.S. Pat. No. 5,284,935 and related patents).

Antigenic determinants may be isolated from an organism according to standard purification methods, for example, as described above. In addition, methods of protein purification are provided by see Deutscher, M. P. *Methods in Enzymology Vol.* 182: *Guide to Protein Purification,* Academic Press, Inc. N.Y. (1990). Alternatively the antigenic determinants may be recombinantly expressed (either alone, in combination with the MHC, or with the MHC/signal transduction molecule chimera) according to standard methods well known to those of skill in the art (see, e.g. Sambrook, supra.).

Nucleic acid sequences encoding polypeptide antigenic determinants of autoimmune diseases may be identified in the same manner as nucleic acid sequences encoding MHC molecules. As indicated above, this involves identifying and isolating the particular antigenic determinant (e.g. myelin basic protein). The amino acid sequence of the polypeptide may be determined directly (e.g. via Edmund degradation). Once the amino acid sequence encoding the protein is known nucleic acid sequences encoding the protein may be chemically synthesized or isolated from a cDNA library using the methods described above.

Alternatively, the nucleic acid sequences of a large number of antigenic determinants are already known and a number are commercially available. For example, the nucleic acid sequences encoding myelin basic protein (MBP) and type III collagen, the antigenic determinants for multiple sclerosis and rheumatoid arthritis respectively, are generally known.

C) Transfection and Culture of Cells Expressing Target Molecule/Signal Transduction Molecule Chimeras As indicated above, methods of producing nucleic acid sequences encoding target molecule/signal transduction molecule chimeras, transfecting cells with vectors containing these nucleic acids and culturing the transfected cells such that they express the encoded chimeras are well known to those of skill in the art. Thus, for example, Moritz et al.,

*Proc. Natl. Acad. Sci. USA,* 91: 4318–4322 (1994), Romeo et al. *Cell.* 64: 1037–1046 (1991), Eshar et al., *Proc. Natl. Acad. Sci. USA,* 90: 720–724 (1993), Capon et al. U.S. Pat. No. 5,359,046, Howard et al., *J. Exp. Med.,* 176: 139–145 (1992) Letourneur et al., *Proc. Natl. Acad. Sci. USA,* 88: 8905–8909 (1991), Weiss et al., *Cold Springs Harbor Symposium on Quantitative Biology* (1992) teach the transfection and culturing of CTLs, NK cells, T cell hybridomas, and hematopoietic stem cells. Particularly preferred cells include CTLs, NK cells, and hematopoietic stem cells.

D) Chemically Coupled Chimeras

While, in a preferred embodiment, the target-signal transducing molecules are preferably recombinantly expressed as a single chain fusion protein, the target molecule may alternatively be chemically linked to the signal transduction molecule. This is particularly advantageous where the target molecule is, for example, a nucleic acid, and not a polypeptide.

Using this approach, the signal transduction molecule is expressed in the as described above and the target molecule is then chemically linked to the extracellular domain of the transduction molecule, either directly or through a linker. The extracellular domain of the signal transduction molecule may be modified (e.g. with the addition of cysteines) to facilitate the subsequent linkage (e.g. through a disulfide linkage).

The procedure for attaching a targeting molecule to the signal transduction molecule will vary according to the chemical structure of the target molecule. Polypeptides typically contain variety of functional groups; e.g., carboxylic acid (COOH) or free amine (—$NH_2$) groups, which are available for reaction with a suitable functional group on the extracellular domain of the signal transduction molecule to bind the target molecule thereto.

Alternatively, the target molecule and/or signal transduction molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the target molecule is a polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a target molecule and another group reactive with the signal transduction molecule may be used to form the desired conjugate. Alternatively, derivatization may involve chemical treatment of the target molecule, e.g., glycol cleavage of the sugar moiety of a glycoprotein with periodate to generate free aldehyde groups. The free aldehyde groups on the glycoprotein may be reacted with free amine or hydrazine groups on the linker to bind the target thereto. (See U.S. Pat. No. 4,671,958). Procedures for generation of free sulfhydryl groups on polypeptides are also known (See U.S. Pat. No. 4,659,839).

Many procedures and linker molecules for attachment of various target compounds including metal chelates, nucleic acids, fatty acids, and the like to polypeptides are well known (see, e.g. European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071–4075 (1987)). In particular, such conjugation methods are particularly well developed for the formation of immunoconjugates, but may easily be modified for conjugation to the signal transduction molecule. Means of conjugating antibodies, and other polypeptides, may be found in Chapter 4 of *Monoclonal Antibodies: Principles and Applications*, Birch & Lennox, eds. John Wiley & Sons, Inc. N.Y. (1995); *Monoclonal Antibody-Toxin Conjugates: Aiming the Magic Bullet*, Thorpe et al., *Monoclonal Antibodies in Clinical Medicine*, Academic Press, pp. 168–190 (1982), Waldmann, *Science,* 252: 1657 (1991), U.S. Pat. Nos. 4,545,985 and 4,894,443.

V. Assays for Efficacy of Treatment

Numerous combinations of target molecule, signal transduction molecule and killer cell type are suitable for the practice of this invention. However, some combinations of these elements (e.g. MHC/ζ chimera in a CTL or NK cell) are particularly effective and hence preferred. Identification of particularly preferred constructs for a particular application by preparing a particular cell containing a target molecule/signal transduction molecule and then assaying that cell for efficacy in that particular application. In particular, where a previously untried target molecule is to be used, it is desirable to assay the efficacy of that molecule as a suitable target when present on particular desired cell type. Suitable assays for evaluation of inhibition of the graft rejection response, mitigation of the autoimmune response, or improvements in B cell presentation are well known to those of skill in the art. However, some examples are provided below.

A) Assay for Graft Rejection

The efficacy of killer cells comprising MHC/signal transduction chimeras in preventing graft rejection is easily assayed. Test mice are infused with killer cells bearing the chimeric molecule. The mice are then engrafted with skin expressing the identical MHC as expressed by the killer cell. Simply, skin is harvested from donor animals expressing the desired MHC and is prepared for grafting by removal of extraneous tissue. The recipient animal is anesthetized and a graft bed is created surgically by removing skin down to the muscle fascia, the paniculus carnosus. The skin graft is placed on the bed and held in place by surgical dressings. The animal is bandaged for seven to nine days. On removal of the bandages the graft is inspected daily until rejection. Rejection is visually obvious as the healthy epidermal tissue is replaced by scab and then by scar.

An assay for in vivo graft rejection involving human cells and human tissues is the SCID-Hu model in which human mature lymphoid populations are injected into immunodeficient SCID mice. Such populations survive and are capable of mediating some immune responses. Thus, mice engrafted with recipient lymphoid cells and engrafted with skin from the donor are expected to reject such skin. However, infusion of recipient "killer" cells expressing donor MHC-signal transduction molecule chimeras abrogates or markedly delays rejection.

In lieu of in vivo assays, killer cells expressing the MHC/signal transduction chimera are evaluated for their ability to modify alloreactive recipient T cells by testing in vitro. Culture of recipient lymphocytes with irradiated donor cells for 5 days produces 1) enhanced proliferation of recipient T cells, 2) cytolytic T cells, and 3) IL-2 secretion from T helper cells. Such responses are inhibited by co-culture with recipient killer cells transfected with donor MHC/signal transduction molecule chimeras.

B) Autoimmune diseases

The following are well known model systems for autoimmune diseases which can be used to evaluate the effects of the killer cells of the invention on these conditions.

1) Systemic Lupus Erythematosus (SLE)

$F_1$ hybrids of autoimmune New Zealand black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to SLE in humans (Knight el al., *J. Exp. Med.* 147:1653 (1978)).

In both the human and murine forms of the disease, a strong association with MHC gene products has been reported. HLA-DR2 and HLA-DR3 individuals are at a higher risk than the general population to develop SLE (Reinertsen et al., *N. Engl. J. Med* 299: 515 (1970), while in NZB/W $F_1$ mice ($H-2^{d/u}$), a gene linked to the h-$2^u$ haplotype derived from the NZW parent contributes to the development of the lupus-like nephritis.

The effect of the treatment with the modified cells of this invention can be measured by survival rates and by the progress of development of the symptoms such as proteinuria. Proteinuria is measured calorimetrically by the use of Uristix (Miles Laboratories, Inc., Elkhart, Ind.), giving an approximation of proteinuria as follows: trace, 10 mg/dl; 1+, 30 mg/dl; 100 mg/dl; 3+, 300 mg/dl; and 4+, 1000 mg/dl. Delay in the development of high grade proteinuria is indicative of the efficacy of the cells of this invention.

2) Myasthenia Gravis (MG)

Myasthenia gravis is one of several human autoimmune diseases linked to HLA-D (Safenberg el al., *Tissue Antigens* 12: 136 (1978); McDevitt el al., *Arth. Rheum.* 20: 59 (1977)). In MG, antibodies to the acetyl choline receptors (AcChoR) impair neuromuscular transmission by mediating loss of AcChoR in the postsynaptic membrane.

SJL/J female mice are a model system for human MG. In these animals, experimental autoimmune myasthenia gravis (EAMG) is induced by immunizing the mice with soluble AcChoR protein from another species. Susceptibility to EAMG is linked in part to the MHC and has been mapped to the region within H-2 (Christadoss el al., *J. Immunol.* 123: 2540 (1978)).

AcChoR protein is purified from *Torpedo californica* and assayed according to the method of Waldor et al., *Proc. Natl. Acad. Sci. (USA)* 80: 2713 (1983). Emulsified AcChoR, 15 μg in complete Freund adjuvant, is injected intradermally among six sites on the back, the hind foot pads, and the base of the tail. Animals are reimmunized with this same regimen 4 weeks later.

Evaluation can be made by measurement of anti-AcChoR antibodies, Anti-AcChoR antibody levels are measured by a microliter ELISA assay as described in Waldor el al., supra. The standard reagent volume is 50 μL per well. Reagents are usually incubated in the wells for 2 hr at RT. Five μg of AcChoR diluted in bicarbonate buffer, pH 9.6, is added to each well. After incubation with AcChoR, the plates are rinsed four times with a wash solution consisting of phosphate-buffer saline containing 0.05% Tween and 0.05% $NaN_3$. Mouse sera are diluted in 0.01M PBS (pH 7.2), 1.5 mfr $MgCl_2$, 2.0 mM 2-mercaptoethanol, 0.05% Tween-80, 0.05% $NaN_3$ (P-Tween buffer) and incubated on the plate.

After the plate is washed, beta-galactosidase-conjugated sheep anti-mouse antibody diluted in P-Tween buffer is added to each well. After a final washing, the enzyme substrate, p-nitrophenyl-galctopyranoside is added to the plate, and the degree of substrate catalysis is determined from the absorbance at 405 nm after 1 hr.

Anti-AcChoR antibodies are expected to be present in the immunized with AcChoR mice as compared to nonimmunized mice. Treatment with the modified cells of this invention is expected to significantly reduce the titer of anti-AcChoR antibodies in the immunized mice.

The effect of treatment with the cells of this invention on clinical EAMG can also be assessed. Myasthenia symptoms include a characteristic hunched posture with drooping of the head and neck, exaggerated arching of the back, splayed limbs, abnormal walking, and difficulty in righting. Mild symptoms are present after a standard stress test, and should be ameliorated by administration of killer cells after a period of time after which antibody titer has fallen.

3) Rheumatoid Arthritis (RA)

In humans, susceptibility to rheumatoid arthritis is associated with HLA D/DR. The immune response in mice to native type II collagen has been used to establish an experimental model for arthritis with a number of histological and pathological features resembling human RA. Susceptibility to collagen-induced arthritis (CIA) in mice has been mapped to the H-2 I region, particularly the I-A subregion (Huse el al., *Fed. Proc.* 43: 1820 (1984)).

Mice from a susceptible strain, DBA-1 are caused to have CIA by treatment of the mice with native type II collagen, using the technique described in Wooley and Luthra, *J. Immunol.* 134: 2366 (1985).

In another model, adjuvant arthritis in rats is an experimental model for human arthritis, and a prototype of autoimmune arthritis triggered by bacterial antigens (Holoschitz et al., *Prospects of Immunology* (CRC Press) ( 1986); Pearson *Arthritis Rheum.* 7: 80 (1964). The disease results from a cell-mediated immune response, as evidenced by its transmissibility by a clone of T cells which were reactive against the adjuvant (MT); the target self-antigen in the disease, based upon studies with the same cloned cells, appears to be part(s) of a proteoglycan molecule of cartilage.

Adjuvant disease in rats is produced as described by Pearson, supra, i.e., by a single injection of Freund's adjuvant (killed tubercle bacilli or chemical fractions of it, mineral oil, and an emulsifying agent) given into several depot sites, preferably intracutaneously or into a paw or the base of the tail. The adjuvant is given in the absence of other antigens.

To assay efficacy of the modified cells of this invention, the effect of treatment on manifestations of the disease are monitored. These manifestations are histopathological, and include an acute and subacute synovitis with proliferation of synovial lining cells, predominantly a mononuclear infiltration of the articular and particular tissues, the invasion of bone and articular cartilage by connective tissue pannus, and periosteal new bone formation, especially adjacent to affected joints. In severe or chronic cases, destructive changes occur, as do fibrous or bony ankylosis. These histopathological symptoms are expected to appear in control animals at about 12 days after sensitization to the Freund's adjuvant.

4) Insulin Dependent Diabetes Mellitus (IDDM)

IDDM is observed as a consequence of the selective destruction of insulin-secreting cells within the Islets of Langerhans of the pancreas. Involvement of the immune system in this disease is suggested by morphologic evidence of early infiltration of the Islets by mononuclear cells, by the detection of anti-islet cell antibodies, by the high frequency of HLA-DR3 and -DR4 alleles in IDDM populations, and by clinical associations between IDDM and various autoimmune diseases.

An animal model for spontaneous IDDM and thyroiditis has been developed in the BB rat. As in humans, the rat disease is controlled, in part, by the genes encoding the MHC antigens, is characterized by islet infiltration, and is associated with the presence of anti-islet antibodies. The I-E equivalent Class II MHC antigens appear to be involved in manifestation of the autoimmune diseases in the BB rat (Biotard et al., *Proc. Natl. Acad. Sci. USA* 82: 6627 (1985)).

In morphologic evaluation, insulitis is characterized by the presence of mononuclear inflammatory cells within the islets. Thyroiditis is characterized by focal interstitial lymphocytic infiltrate within the thyroid gland, as a minimum criterion. Most severe cases show diffuse extensive lymphocytic infiltrates, disruption of acini, fibrosis, and focal Hurthle call change (see Biotard et al, supra).

Treatment of the BB rats with killer cells of this invention is expected to ameliorate or prevent the manifestation of the clinical and morphological symptoms associated with IDDM and thyroiditis.

In another spontaneous model, the NOD mouse strain (H-2$K^dD^b$) is a murine model for autoimmune IDDM. The disease in these animals is characterized by anti-islet cell antibodies, severe insulitis, and evidence for autoimmune destruction of the beta-cells (Kanazawa et al., *Diabetologia* 27: 113 (1984)). The disease can be passively transferred with lymphocytes and prevented by treatment with cyclosporin-A (Ikehara, et al., *Proc. Natl Acad. Sci. USA* 82: 7743 (1985); Mori, et al. *Diabetologia* 29: 244 (1986)). Untreated animals develop profound glucose intolerance and ketosis and succumb within weeks of the onset of the disease. Seventy to ninety percent of female and 20–30% of male animals develop diabetes within the first six months of life. Breeding studies have defined at least two genetic loci responsible for disease susceptibility, one of which maps to the MHC. Characterization of NOD Class II antigens at both the serologic and molecular level suggest that the susceptibility to autoimmune disease is linked to I-$A_B$ (Acha-Orbea et al. *Proc. Natl Scad. Sci. USA,* 84: 235 (1987)).

Treatment of female NOD mice with killer cells of this invention is expected to lengthen the time before the onset of diabetes and/or to ameliorate or prevent the disease.

5) Experimental Allergic Encephalomyelitis (EAE)

Experimental allergic encephalomyelitis (EAE) is an induced autoimmune disease of the central nervous system which mimics in many respects the human disease of multiple sclerosis (MS). The disease can be induced in many species, including mice and rats.

The disease is characterized by the acute onset of paralysis. Perivascular infiltration by mononuclear cells in the CNS is observed in both mice and rats. Methods of inducing the disease, as well as symptomology (for a review see Aranson at pp 399–427 in Aranson in *The Autoimmune Diseases* Rose and Mackay, eds. Academic Press, Inc., N.Y. (1985) and Acha-Orbea et al. *Ann. Rev. Imm.* 7: 377–405 (1989)).

One of the genes mediating susceptibility is localized in the MHC class II region (Moore et al. *J. Immunol.* 124: 1815–1820 (1980)). The best analyzed encephalitogenic protein is myelin basic protein (MBP), but other encephalitogenic antigens are found in the brain. The immunogenic epitopes have been mapped (see Acha-Orbea et al., supra.). In the PL mouse strains (H-2$^u$) two encephalitogenic peptides in MBP have been characterized: MBP peptide p35–47 (MBP 35–47), and acetylated (MBP 1–9).

The effect of the killer cells of this invention on ameliorating disease symptoms in individuals in which EAE has been induced can be measured by survival rates, and by the progress of the development of symptoms.

The foregoing list of assays is intended to be illustrative, but not limiting. One of skill in the art will readily appreciate the application of other model systems for screening the modified killer cells of this invention for efficacy in the treatment of autoimmune diseases.

C) Assays for Improved B Cell Presentation

Assays measuring T cell proliferation, or T cell function (such as IL-2 secretion) as a function of B cell presentation are sufficient to assay improved B cell presentation of antigen. Tumor specific antigens presented by B cells bearing the MHC/signal transduction molecule chimeras cause enhanced proliferation and IL-2 secretion of tumor specific T cells over that elicited by B cells lacking the chimeric molecule. Relative efficacy of various B cell constructs may be compared by comparing T cell proliferation of IL-2 secretion induced by presentation with the various B cell constructs. Means of measuring IL-2 secretion of T cell proliferation are well known to those of skill in the art (see, e.g. Example 1).

VI. T-Cell Specific Promoters in Tolerance Induction

In another embodiment, this invention provides an alternative method of inducing tolerance. It was discovered that MHC/ζ constructs placed into a vector in which the promoter and enhancer elements are T cell specific (e.g., the CD2 promoter which mediates expression of the construct on maturing T and B cells Greaves, el al. *Cell* 56: 979–986 (1989)). Expression of the MHC/ζ construct was minimal on bone marrow cells (<5%) whereas MHC genes placed under control of the MHC promoter mediates high level expression in bone marrow cells (>60%). Thus bone marrow cells transfected with MHC under control of T cell promoters will not be recognized as foreign, because so few bone marrow will express the MHC, and not subjected to rejection.

Instead, MHC will be expressed on maturing thymocytes in the thymus, where they mediate deletion or anergy of developing MHC reactive T cells. In contrast bone marrow cells transfected with MIC under MHC promoter/enhancer elements will be recognized as foreign and subjected to rejection responses.

Experimentally, using transgenic mice, this was observed to be the case (see Example 5). Mice lightly irradiated (300 Gy) and given bone marrow from $D^d$ζ transgenic mice (with the $D^d$ζ under control of the T cell specific CD2 promoter) became chimeric for expression of $D^d$ in lymphoid populations and experience prolonged survival of skin grafts expressing MHC class I $D^d$ whereas mice similarly treated and given bone marrow from p$D^d$1 transgenic mice (with MHC I $D^d$ under control of the MHC promoter) failed to develop chimerism and were primed, as shown by accelerated rejection of Dd expressing skin grafts over naive animals (Table 4).

Thus, promoter/enhancer elements causing T or B cell specific expression offer a potent tool to induce transplantation tolerance. In one embodiment, a patient to receive a kidney graft or partial liver graft from a living related donor would have bone marrow removed. The hematopoietic progenitor cells would be transfected with foreign HLA or HLA/ζ of the donor placed in a T cell specific promoter/enhancer containing vector. The recipient would be given sub-lethal conditioning and infused with the transfected syngeneic bone marrow. Following several weeks, the patient would be assessed for chimerism and tolerance and would be transplanted with the organ graft.

One of skill in the art will appreciate that the HLA will preferably be the HLA characteristic of the transplant. This would generally require that a specific vector construct be engineered for each donor. Economies of scale can be achieved, however, where numerous donors possess the same HLA. This technique is thus particularly well suited to induction of xenograft tolerance where the donor organisms are inbred or otherwise altered to consistently express the same HLA. Transgenic animals (e.g., primates, porcines) modified to express exogenous MHC are particularly well suited to this application. Means of production of such animals are well known to those of skill in the art.

While the T cell "specific" CD2 promoter is suitable for this purpose, this promoter also mediates expression in some B cells. Other promoters showing greater T cell specificity are more preferred. Such promoters are well known to those of skill in the art and include, but are not limited to Lck promoters (Perlmutter el al. *JEM* 173: 383–393 (1991)), CD4 promoters (Littman et al., *Mol and Cell Biology* 11: 5506–5515), and CD3 promoters (see, e.g., Georgopoulos et al. *EMBO J.,* 7: 2401 (1988), Lee et al. J. E. M., 175: 1013–1025 (1992) and Killeen et al. *Nature,* 364: 729–732), and the like. Methods of identifying T cell specific promoters are well known to those of skill in the art (Perlmutter et al., Littman el al., Georgopoulos et al., Lee el al., and Killeen et al. supra., and references cited therein.)

VII. Pharmacological Compositions

The cells bearing target molecule/signal transduction chimeras of this invention are particularly usefull for parenteral administration, such as intravenous administration or administration into a body cavity or lumen of an organ. Particularly where the "killer" cell is a hematopoietic stem cell administration may be into the bone marrow (vide supra.).

The compositions for administration will commonly comprise a solution of the modified cells suspended in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about $1 \times 10^6$/kg body weight cells per patient per day. Actual methods for preparing parenterally administrable compositions will be known or apparent to those skilled in the art and are described in more detail in such publications as *Reminton's Pharmaceutical Science,* 15th ed., Mack Publishing Company, Easton, Pa. (I 980).

The compositions containing the cells of this invention cocktail therapeutic (i.e., with other drugs and/or proteins) can be administered for therapeutic treatments. In therapeutic applications, compositions are administered to a patient suffering from graft rejection or an autoimmune disease, in an amount sufficient eliminate or to inhibit the graft rejection response or to at least partially arrest symptoms of the autoimmune disease. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the cells of this invention to effectively treat the patient.

VIII. Kits

In another embodiment, this invention provides for kits for the treatment or prevention of graft rejection or for the treatment of an autoimmune disease. Kits will typically comprise a killer cell of this invention bearing a target molecule/signal transduction molecule chimera (e.g. a CTL expressing an HLA/$\zeta$ fusion protein). In addition the kits will typically include instructional materials disclosing means of use of chimeric molecule (e.g. as a cytotoxin, for detection of tumor cells, to augment an immune response, etc.).

Alternatively, the kits may include a nucleic acid expression cassette encoding an MHC or HLA/$\zeta$ fusion protein or, alternatively, where it is desired to just induce recipient anergy, the kit may simply include the above-described MHC or HLA under control of a T cell promoter (e.g., CD2 promoter, Lck promoter, CD4 promoter). The construct can simply include a cassette encoding a $\zeta$ chain, where the expression cassette contains appropriate restriction sites for the rapid and easy insertion of a nucleic acid sequence encoding an antigen (e.g., a HLA). The expression cassette will be adapted for rapid transfection of cells from a potential recipient of the graft.

The kits may also include additional components to facilitate the particular application for which the kit is designed. Thus, for example, where a kit contains a killer cell designed to treat graft rejection (e.g. having the graft MHC molecule as a target molecule) the kit may additionally include the graft tissue or organ itself. The organ may represent a xenograft from an inbred strain or an organism transgenically modified to express a specific MHC. The kit may additionally contain means of expanding, culturing and administering the cells. The kit may also include vectors for modifying cells obtained from the patient so that they express one of the signal transduction molecule chimeras of this invention. The kits may additionally include buffers and other reagents routinely used for the practice of a particular method. Such kits and appropriate contents are well known to those of skill in the

EXAMPLES

The following examples are offered to illustrate, but not to limit the present invention.

Example 1

Construction and expression of a plasmids encoding, an MHC/$\zeta$ fusion proteins A) Construction of $D^d\zeta$ A $D^d$ cDNA encoding mouse class I MHC molecule (see SEQ ID NO:11) was altered by truncating the cDNA at base pair 1023 to remove the intracellular domain and a portion of the transmembrane region. This was accomplished by polymerase chain reaction (PCR) using the $D^d$ 5' primer 5'-TAAATTCTCGAGGGATCCCAGATGGGGGCG-3' (SEQ ID NO:1) and the $D^d$ 3' primer:

5'-CTGCACGAATTCTCTCCTCCTCCTCATCAC-3' (SEQ ID NO:2). The $D^d$ primer is complementary to the 5' end of the $D^d$ cDNA, while the $D^d$ primer is complementary to base pairs 1006–1023 of the $D^d$ cDNA and adds a new EcoRI site at the 3' end of the truncated gene. The PCR product was digested with BamHI and EcoRI and ligated into the BamHI/EcoRI site of plasmid pSP72 (Promega, Madison, Wisc.). The resulting plasmid, bearing a DNA encoding the alpha 1, alpha 2 and alpha 3 extracellular domains of $D^d$ is referred to as $D^d$ pSP72.

The murine C cDNA was amplified from the pGEM-7Zf (+) (Weisman, el al., *Science*, 239: 1018 (1988)) using PCR primers A 5'-TCGTATGAATTCGCAAAATTCAGCAG GAGTGCAGAG-3' and B (SEQ ID NO:3) and B 5'-CTAGCTAGATCTAAGCTTGCATGCCTGCAGGTC GAC-3' (SEQ ID NO:4). Primer A, the 5' primer is complementary to the sequence that begins 4 bp to the 3' of the zeta transmembrane region. This primer also includes an EcoRI restriction enzyme recognition site with an EcoRI site to the 5' end of the PCR product. Primer B, the 3' primer, is complementary to a sequence in the multiple cloning site of the vector and adds a BglII site to the 3' end of the PCR product. After PCR, the amplification product was digested with EcoRI and BglII. The fragment was ligated into the EcoRI/BglII site of $D^d$-pSP72. The resulting construct was termed $D^d$zeta-pSP72.

B) Construction of $D^d\zeta$ using the transmembrane region of $\zeta$

In the construct of Example 1A, the transmembrane originated from the Dd molecule. Because there were no disulfide linkages, this molecule did not have the potential to dimerize (or otherwise associate) with other signaling moieties. Thus, in order to construct a MHC-$\zeta$ fusion is expected to more rapidly and potently mediate activation signals and more rapidly stimulate cellular function, a MHC-$\zeta$ fusion was constructed incorporating the $\zeta$ transmembrane domain rather than the MHC transmembrane domain.

To obtain DNA encoding the extracellular domain of the H-2$L^d$, the DNA encoding the extracellular domain of H-2$D^d$ was PCR amplified from the plasmid pDdSEL.FIX34 plasmid ((see, e.g., Ribaudo and Margulies, *J. Immunol.*, 155: 3481–3493 (1995) and references cited therein). The PCR primers used for the amplification of $D^d$ were as follows: The $D^d$ forward primer was 5-TCAAGC TTGCATGCCTGC-3' (SEQ ID NO:5) which encodes the pSELECT vector and the $D^d$ reverse primer 3'-CTCTACCCCGTTCCTCCTA-5' (SEQ ID NO:6), which encodes the 3' end of the extracellular domain of $D^d$. The reverse primer introduces and EcoR V site at the 3' end of the PCR product.

The transmembrane and intracellular domains of the murine $\zeta$ molecule were obtained by PCR amplification. A murine $\zeta$ cDNA clone formed was used as the PCR template. The primer pair for the $\zeta$ molecule consisted of the following: the $\zeta$ forward primer 5'-GATCCCAAACTCTGCTAC TTGCTAGAT-3' (SEQ ID NO:7), which corresponds to the junction between the extracellular and transmembrane region of $\zeta$, and the $\zeta$ reverse primer 3'-CGATTG TCGGTCCCGTAAAGATCTAGT-5' (SEQ ID NO:8), which encodes the 3' end of the cDNA coding sequence and a portion of the 3' untranslated region. The reverse primer introduces an Xba I site at the 3' end of the PCR product.

The $D^d\zeta$ construct is placed into the expression vector pcDNA3 (Invitrogen, San Diego, Calif., USA).

The construction of the fusion molecule then proceeds in one of two ways:

Scheme 1:

The $D^d$ and $\zeta$ nucleic acid sequences are PCR amplified as described above. The $D^d$PCR product is then digested with BamH I resulting in a BamH I sticky end at the 3' end of each piece of DNA. The $\zeta$ PCR product is then cut with Xba I resulting in a 3' Xba I sticky end. The pcDNA3 vector is then cut with both BamH I and Xba I and pcDNA3+$D^d$+$\zeta$ are ligated together using standard methods to produce a construct encoding a $D^d/\zeta$ fusion protein.

Scheme 2:

The $D^d$ and $\zeta$ nucleic acid sequences are PCR amplified as described above. The $D^d$ PCR product is then digested with BamH I resulting in a BamHI sticky end at the 3' end of each piece of DNA. The pcDNA3 is cut with BamH I and then pcDNA3+$D^d$ are ligated together according to standard methods. The clones with inserts are isolated. The $\zeta$ PCR product is then digested with Xba I and the pcDNA3/$D^d$ construct is digested with EcoR V and Xba I. Finally, pcDNA3/$D^d$ is ligated with s to form a plasmid encoding $D^d/\zeta$ chimera.

C) Construction of $L^d\zeta$

To obtain DNA encoding the extracellular domain of the H-2$L^d$, DNA encoding the extracellular domain of H-2$L^d$ was PCR amplified from the plasmid p$L^d$SEL. I (see, e.g., Ribaudo and Margulies, *J. Immunol.*, 155: 3481–3493 (1995) and references cited therein). The PCR primers used for amplification of $L^d$ were as follows: The $L^d$ forward primer, 5'-GGAGGAGGCAGGTGACTA-3' (SEQ ID NO:9) which encodes the pSELECT vector sequence, and the $L^d$ reverse primer 3'-GAGTGGGACTCTACCCTA-5' (SEQ ID NO:10) which encodes the 3' end of the $L^d$ extracellular domain. The reverse primer also introduces and EcoR V site at the 3' end of the PCR product.

The remainder of the construction proceeds as described above in Section B, substituting the $L^d$ PCR product for the $D^d$ PCR product.

Example 2

Measurement of cell activation by recognition of $D^d/\zeta$ chimeras

Jurkat cells, a human IL-2 secreting T cell tumor line, were transfected with vectors encoding mouse class I MHC $D^d$ or $D^d/\zeta$ molecules (described above). To test whether recognition of the $D^d$ moiety of the $D^d/\zeta$ chimera would trigger IL-2 secretion, the transfected Jurkat cells were cultured with anti-$D^d$ monoclonal antibody, with OKT3, an anti-CD3 antibody used as a positive control, or without antibody, a negative control, with and without phorpol myristic acetate (PMA), a co-stimulatory molecule, for 24 hours and the cell free supernatant was collected. The supernatant was added to an IL-2 dependent cell line (CTLL-2) to test proliferation. Significant levels of IL-2 enhance proliferation of CTLL-2 cells. As seen in Tables 2 and 3, untransfected Jurkat cells or Jurkat cells expressing $D^d$ alone do not enhance proliferation of CTLL-2 when stimulated (recognized) by anti-$D^d$ monoclonal antibody, indicating that the monoclonal antibody binding of $D^d$ did not trigger IL-2 secretion. However, Jurkat cells expressing the $D^d/\zeta$ chimera manifested a two to ten fold increase in proliferation of CTLI-2 cells indicating that anti-$D^d$ monoclonal antibody triggered IL-2 secretion (activation of the T cell).

TABLE 2

Proliferation of CTLL-2 cells

| Cell Line | Antibody | PMA | Proliferation (CPM) |
|---|---|---|---|
| Jurkat: | — | − | 1,231 ± 81 |
|  | — | + | 1,068 ± 35 |
|  | $D^d$ | − | 1,254 ± 73 |
|  | $D^d$ | + | 2,440 ± 295 |
|  | OKT3 | − | 1,177 ± 89 |
|  | OKT3 | + | 2,204 ± 199 |
| J11-6 ($D^d/\zeta$): | — | − | 525 ± 127 |
|  | — | + | 2,766 ± 75 |
|  | $D^d$ | − | 338 ± 156 |
|  | $D^d$ | + | 26,827 ± 2,298 |
|  | $D^d/\zeta$ | − | 676 ± 262 |
|  | $D^d/\zeta$ | + | 27,670 ± 1,765 |

TABLE 3

Proliferation of CTLL-2 cells

| Cell Line | Antibody | PMA | Proliferation (CPM) |
|---|---|---|---|
| #19 ($D^d$): | — | − | 279 ± 105 |
|  | — | + | 4,517 ± 153 |
|  | $D^d$ | − | 492 ± 199 |
|  | $D^d$ | + | 5,518 ± 328 |
|  | OKT3 | − | 9,534 ± 2,529 |
|  | OKT3 | + | 10,912 ± 592 |
| J11-6 ($D^d/\zeta$): | — | − | 647 ± 191 |
|  | — | + | 7,041 ± 220 |
|  | $D^d$ | − | 361 ± 151 |
|  | $D^d$ | + | 16,679 ± 312 |
|  | $D^d/\zeta$ | − | 3,243 ± 685 |
|  | $D^d/\zeta$ | + | 34,043 ± 172 |

In a second series of experiments, IL-2 secreting Jurkat cell lines were transfected with either $D^d\zeta$, $D^d$ in the absence of a signaling molecule, or a truncated $D^d$ (truncated at the transmembrane region to remove any signaling potential) all under control of the CD2 promoter. The cells were incubated with PMA (10 ng/µL) and $D^d$ specific mAb, or OKT3 mAb for 24 hours in the presence of an anti-mouse Ig antibody. Cell free supernatants from these cultures were assayed for IL-2 by proliferation of CTLL-2 cells (an IL-2 dependent cell line) as follows: 50 µL of CTLL-2 cells ($5 \times 10^4$/ml) were incubated with 50 µL of the supernatant from the Jurkat cultures for 24 hours. The samples were pulsed with [$^3$H] TdR for the last 6 hours of culture. The [$^3$H]TdR uptake was determined in a betaplate counter. The cells were incubated with mAb against $D^d$ or against the CD3 portion of the TcR (positive control) and further cross linked using an anti-Ig antibody.

A remarkable enhancement of IL-2 production by cells expressing $D^d/\zeta$ was observed with a 4.5–10 fold increase in cytokine production over that of cells expressing $D^d$ alone or truncated $D^d$ (Table 4). In contrast, all clones responded comparably to ligation of the CD3 element of the T cell receptor.

Cross linking of the $D^d$ moiety of $D^d/\zeta$ molecules also directly stimulated proliferation of cells expressing it. Whole lymphoid populations from $D^d/\zeta$ or $pD^d1$ transgenic mice were stimulated by a panel of mAbs for 48 hours and proliferation assessed. Lymphoid populations were harvested from spleen of transgenic $D^d/\zeta$ or $pD^d1$ mice and incubated for 72 hours in the absence of mAb, or in the presence of anti-$D^d$ mAb, anti-CD3 mAb, anti-CD8 mAb, or combinations as shown in Table 5. Following incubation, cells were pulsed with [3H]TdR and harvested 12 hours later.

TABLE 4

$D^d/\zeta$ expressing Jurkat cells produce greater amounts of IL-2 than cells expressing $D^d$ in the absence of a signaling molecule

| Cell Line | Antibody + PMA | Experiment 1 Mean ± SD | Experiment 2 Mean ± SD |
|---|---|---|---|
| JurKat | None | 3,880 ± 4,177 | 5,076 ± 2,018 |
| $D^d/\zeta$ | None | 4,463 ± 69 | 5,270 ± 1,560 |
| $D^d$ full length | None | 2,883 ± 331 | 5,243 ± 3,326 |
| $D^d$ tailess | None | 3,682 ± 1,077 | 4,018 ± 992 |
| JurKat | $D^d$ (34-2-12) | 2,783 ± 379 | 1,900 ± 1,171 |
| $D^d/\zeta$ | $D^d$ | 54,888 ± 8,492 | 24,120 ± 7,786 |
| $D^d$ full length | $D^d$ | 5,798 ± 1,330 | 5,536 ± 3,055 |
| $D^d$ tailess | $D^d$ | 2,695 ± 939 | 4,664 ± 2,904 |
| JurKat | OKT3 | 60,279 ± 3,173 | 25,32 ± 1,580 |
| $D^d/\zeta$ | OKT3 | 64,843 ± 4,927 | 51,391 ± 2,021 |
| $D^d$ full length | OKT3 | 58,259 ± 5,232 | 66,821 ± 4,071 |
| $D^d$ tailess | OKT3 | 51,438 ± 5,342 | 36,468 ± 7,363 | mAb, anti-CD3 mAb, anti-CD8 mAb, or combinations as shown in TABLE 5. Following incubation, cells were pulsed with [3H]TdR and harvested 12 hours later.

As can be seen in Table 5, comparable proliferation was seen at baseline and in response to CD3 and CD8 mAbs. However, a dramatic enhancement of proliferation was observed in $D^dd/\zeta$ cultures in response to ligation of $D^d$ with or without other mAbs, varying by 10–300 fold over the $D^d$ alone expressing cells. The results of these studies indicate that the presence of the signaling molecule not only enhances the level of function of such cells but also profoundly stimulates expansion of populations expressing the construct.

Based on these findings, the mechanism by which expression of the Dd-zeta construct suppresses allospecific responses to $D^d$ allodeterminants involves inactivation or elimination in vivo of $D^d$ specific T helper or T killer cells by enhanced function of cytolytic T killer cells expressing Dd-zeta, by enhanced cytokine secretion of downregulatory cytokines such as IL-10 by Dd-zeta expressing Th cells, or by a combination of mechanisms.

TABLE 5

Effects of the signaling molecule $\zeta$ on cellular proliferation

| Gene Tx | none | $D^d$ | CD3 | CD8 | $D^d$ + CD8 | $D^d$ + CD8 + CD3 |
|---|---|---|---|---|---|---|
| $D^d$ | 1,024 | 897 | 5,805 | 950 | 1,241 | 24,955 |
| $D^d/\zeta$ | 642 | 303,210 | 8,045 | 589 | 242,164 | 252,744 |

Example 3

Inhibition of Graft Rejection Using $D^d/\zeta$ CTLs

This experiment was designed to test whether adoptive transfer of "killer" lymphocytes expressing allogeneic class I MHC molecules fused to a signal transduction molecule ($D_d/\zeta$ chimeras) differ from lymphocytes expressing only the allogenic class I MHC molecule ($D^d$) with respect to subsequent rejection of skin grafts expressing the same allogeneic MHC class I $D^d$ alloantigen.

Inbred (FVB) mice were transformed with a $D^d$ zeta construct in the human CD2 minigene p29Δ-2(Sal⁻) (Greaves et al. (1989) *Cell,* 56: 979–986) by embryo injection thereby providing a stable line of transgenic mice having lymphocytes that express the $D^d/\zeta$ chimera. One founder line was established and used for all experiments. In these mice $D^d$ is expressed to varying degrees on most T cells and on a subpopulation of B cells. Similarly a control line of mice (pD$^d$1 transgenic mice) was constructed by injection of genomic D$^d$ (containing normal MHC promoter and enhancer elements) into FVB blastocysts. These mice expressed the D$^d$ MHC (without the ζ fusion) at a uniformly high level on all cells of these animals.

FVB mice transgenic for either Dd or D$^d$/ζ were inoculated three times with EL-4 cells at two week intervals. Following the last inoculation, the spleen and lymph nodes were harvested and lymphocytes preparations were made from each tissue. Approximately 20×10$^6$ cells were injected into recipient FVB mice (which are H-2q and hence do not normally express D$^d$). Skin grafts were transplanted 10 days following infusion from the D$^d$ mice to the test and control mice (see, e.g. Rosenberg in *Current Protocols in Immunology*, Coligon el al., ed. Greene Pub. Assoc./Wiley Interscience, N.Y (1991) for skin graft protocols). The time to graft rejection (designated as the point where 80% of the graft was destroyed) was monitored. Animals were monitored daily for graft rejection.

As can be seen in FIG. 1, FVB mice infused with D$^d$ expressing lymphocytes reject skin grafts expressing D$^d$ very rapidly, with a median survival time (MST) of 7 days. In marked contrast, mice infused with lymphocytes expressing D$^d$/ζT had a delayed rejection with a MST of 23.5 days. Thus, expression of the MHC/ζ construct on lymphocyte populations caused a marked difference in the capacity of animals treated with such populations to effect rejection of subsequent skin grafts. These data indicate, taken with the other experiments described herein indicate that MHC/ζ constructs can suppress allospecific responses leading to generation of cytolytic T lymphocytes and graft rejection.

Example 4

Inhibition of Graft Rejection by D$^d$/ζ Transgenic Mice

In the D$^d$/ζ transgenic mice described above, the MHC class I D$^d$ molecule is only expressed on T cell populations and on a subpopulation of B cells because the promoter/enhancer elements driving its expression derive from the human CD2 gene. The D$^d$/ζ transgenic mice (background mouse strain is FVB) fail to reject skin grafts expressing only MHC class I D$^d$ determinants (⅕ rejected) yet reject third party (B6tD8) skin grafts in a time course commensurate with that of normal FVB mice (Table 6, 11.5 vs 10 days median survival time (MST, the time at which 50% of grafts have been rejected). The B6tD8 cells express both MHC class I and II differences as well as minor-histocompatibility differences). In contrast, non-transgenic FVB mice uniformly reject MHC class I disparate D$^d$ skin grafts (MST 15 days).

Lymphoid cells from D$^d$-zeta mice were assessed for cytolytic T killer activity. Spleen cells from D$^d$/ζ transgenic mice that failed to reject pD$^d$1 skin grafts were cultured for 5 days with pD$^d$1 or B6tD8 irradiated (3000 Gy) stimulator cells. Effectors were harvested and killing of P815 (a D$^d$ expressing tumor cell line) and B6tD8 were assessed.

Figure 2:
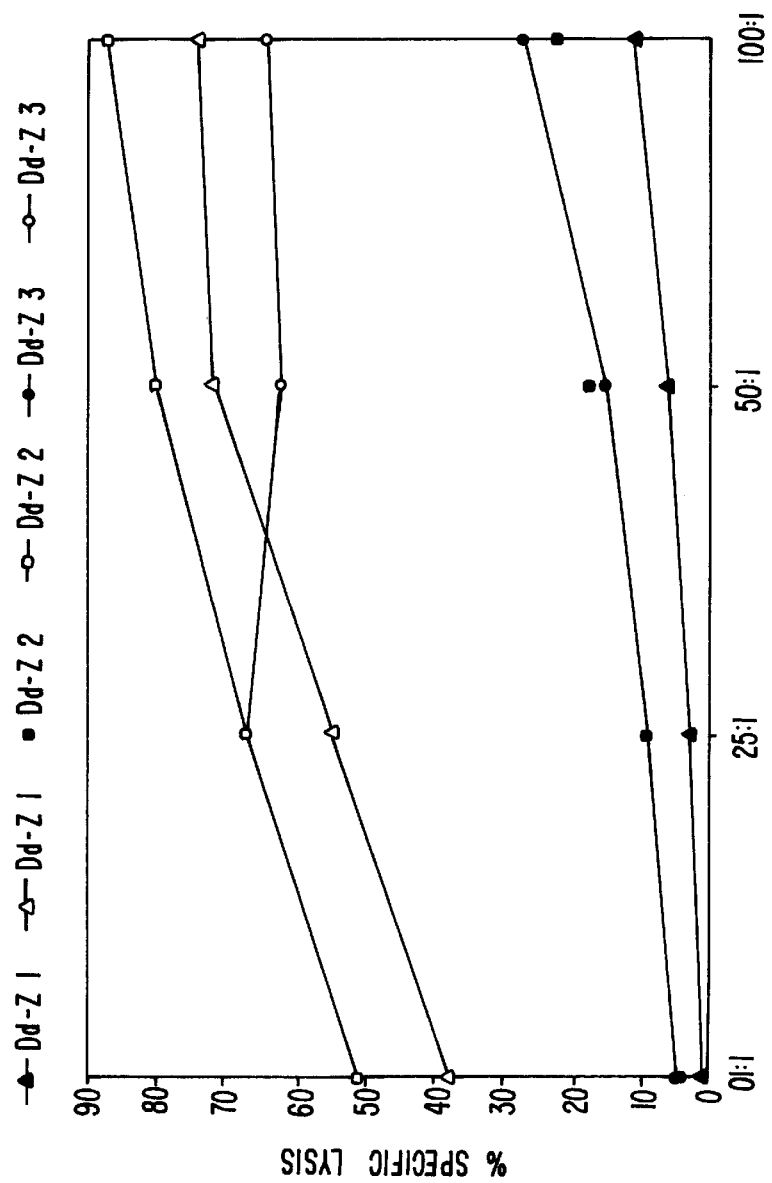
FIG. 2 shows the assessment of cytolytic activity in $D^d/ζ$ transgenic mice. Each pair of symbols refers to a different animal. Open symbols represent $D^d/ζ$ responders stimulated with B6tD8 stimulators and assessed on B6tD8 target cells; closed symbols represent $D^d/ζ$ responders stimulated with $pD^d1$ stimulators and assessed on P815 target cells. E:T is the effector to target ratio.

It was determined that D$^d$/ζ transgenic mice failed to generate significant killer activity to targets expressing only allogeneic D$^d$ determinants, but generated a robust response against third party (B6tD8) allogeneic target cells (FIG. 2).

TABLE 6

D$^d$/ζ transgenic mice or control non-transgenic mice were engrafted with with tail or earskin from pD$^d$1 mice (expressing D$^d$) or with tailskin from B6tD8 mice (expressing multiple MHC class I and II differences as well as minor-histocompatibility differences). Grafts were scored daily until day 60 or 70. MST = median survival time, the time at which 50% of grafts were rejected.

| Host | Donor | Graft Disparity | # Rejected | MST (days) |
| --- | --- | --- | --- | --- |
| FVB: D$^d$ζ | pD$^d$1 | MHC Class I D$^d$ | 0/4 | >70 |
| FVB: D$^d$ζ | pD$^d$1 | MHC Class I D$^d$ | 1/5 | >60 |
| FVB | pD$^d$1 | MHC Class I D$^d$ | 5/5 | 15 |
| FVB: D$^d$ζ | B6tD8 | MHC + minor − H | 4/4 | 11.5 |
| FVB | B6tD8 | MHC + minor − H | 5/5 | 10 |

Example 5

Bone Marrow Transplantation

A second line of evidence that the hybrid zeta chain/MHC construct eliminates or inactivates allospecific D$^d$ reactive lymphocytes came from bone marrow transplantation studies. Non-transgenic FVB mice were lightly irradiated (300 Gy) and 6 hours later transplanted with 20×10$^6$ bone marrow cells from D$^d$ζ (D$^d$-zeta) transgenic mice, from control pDd1 mice, or were not transfused. Bone marrow cells from D$^d$ζ transgenics expressed D$^d$ on less than about 5% of cells (the CD2 promoter drives expression on T cells undergoing maturation events in the thymus, but not on T cell precursors in bone marrow), whereas bone marrow cells from pD$^d$1 mice expressed D$^d$ on greater than 60% of bone marrow cells.

At four weeks post-transplantation, 8/9 D$^d$ ζ transplanted mice contained cells expressing D$^d$ albeit at low levels (about 1–4% of PBLs), whereas only ⅓ of mice transfused with pD$^d$1 bone marrow contained D$^d$ expressing cells.

Five weeks following transfusion, mice were engrafted with a pD$^d$1 skin graft expressing MHC class I D$^d$. As shown in Table 7, prolonged survival of skin grafts was observed in mice transplanted with D$^d$ ζ bone marrow over that of mice transplanted with pD$^d$1 bone marrow and over that of naive non-transgenic mice (MST 32 days versus 18 days, versus 21 days).

Similar results were observed in a second experiment (MST 33 days, versus, 10 days, versus 15 says). Thus, the presence of even small numbers of cells expressing D$^d$ζ markedly delayed rejection of skin grafts expressing D$^d$.

TABLE 7

Bone marrow transplant from D$^d$ζ but not pDd1 transgenic mice prolongs survival of subsequently placed tailskin expressing MHC class I Dd.

| Bone Marrow Donor | Host | Skin Graft | Graft Disparity | # Rejected | MST (days) |
| --- | --- | --- | --- | --- | --- |
| — | FVB | pD$^d$1 | MHClD$^d$ | 3/3 | 21 |
| pD$^d$1 | FVB | pd$^d$1 | MHClD$^d$ | 3/3 | 18 |
| D$^d$ζ | FVB | pd$^d$1 | MHClD$^d$ | 9/9 | 32 |
| — | FVB | pd$^d$1 | MHClD$^d$ | 5/5 | 15 |
| pD$^d$1 | FVB | pd$^d$1 | MHClD$^d$ | 7/7 | 10 |
| D$^d$ζ | FVB | pd$^d$1 | MHClD$^d$ | 9/14 | 33 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference.

Sequence Listing

Sequence ID No:1. A nucleic acid encoding the D^d MHC.

Range: 1 to 1183

```
         10        20        30        40
          .         .         .         .
-------->
GGA TCC CAG ATG GGG GCG ATG GCT CCG CGC ACG CTG CTC CTG CTG CTG 50        60        70        80        90
 .         .         .         .         .
GCG GCC GCC CTG GGT CCG ACT CAG ACC CGC GCT GGC TCA CAC TCG CTG
                                        Gly Ser His Ser Leu>
                                        ___EXON 2 (ALPH____>

100       110       120       130       140
     .         .         .         .         .
AGG TAT TTC GTC ACC GCC GTG TCC CGG CCC GGC TTC GGG GAG CCC CGG
Arg Tyr Phe Val Thr Ala Val Ser Arg Pro Gly Phe Gly Glu Pro Arg>
___a___a___a___a___EXON 2 (ALPHA 1 DOMAIN)_a___a___a___a___a___>

150       160       170       180       190
     .         .         .         .         .
TAC ATG GAA GTC GGC TAC GTG GAC AAC ACG GAG TTC GTG CGC TTC GAC
Tyr Met Glu Val Gly Tyr Val Asp Asn Thr Glu Phe Val Arg Phe Asp>
___a___a___a___a___EXON 2 (ALPHA 1 DOMAIN)_a___a___a___a___a___>

200       210       220       230       240
     .         .         .         .         .
AGC GAC GCG GAG AAT CCG AGA TAT GAG CCG CGG GCG CGG TGG ATA GAG
Ser Asp Ala Glu Asn Pro Arg Tyr Glu Pro Arg Ala Arg Trp Ile Glu>
___a___a___a___a___EXON 2 (ALPHA 1 DOMAIN)_a___a___a___a___a___>

250       260       270       280
     .         .         .         .
CAG GAG GGG CCG GAG TAT TGG GAG CGG GAG ACA CGG AGA GCC AAG GGC
Gln Glu Gly Pro Glu Tyr Trp Glu Arg Glu Thr Arg Arg Ala Lys Gly>
___a___a___a___a___EXON 2 (ALPHA 1 DOMAIN)_a___a___a___a___a___>

290       300       310       320       330
 .         .         .         .         .
AAT GAG CAG AGT TTC CGA GTG GAC CTG AGG ACC GCG CTG CGC TAC TAC
Asn Glu Gln Ser Phe Arg Val Asp Leu Arg Thr Ala Leu Arg Try Tyr>
___a___a___a___a___EXON 2 (ALPHA 1 DOMAIN)_a___a___a___a___a___>

340       350       360       370       380
     .         .         .         .         .
AAC CAG AGC GCG GGC GGC TCT CAC ACA CTC CAG TGG ATG GCT GGC TGT
Asn Gln Ser Ala Gly Gly Ser His Thr Leu Gln Trp Met Ala Gly Cys>
___EXON 2 (ALPH___>
            ___b___b_EXON 3 (ALPHA 2 DOMAIN)___b___b___>

390       400       410       420       430
     .         .         .         .         .
GAC GTG GAG TCG GAC GGG CGC CTC CTC CGC GGG TAC TGG CAG TTC GCC
Asp Val Glu Ser Asp Gly Arg Leu Leu Arg Gly Tyr Trp Gln Phe Ala>
___b___b___b___b___EXON 3 (ALPHA 2 DOMAIN)_b___b___b___b___b___>

440       450       460       470       480
     .         .         .         .         .
TAC GAC GGC TGC GAT TAC ATC GCC CTG AAC GAA GAC CTG AAA ACG TGG
Tyr Asp Gly Cys Asp Tyr Ile Ala Leu Asn Glu Asp Leu Lys Thr Trp>
___b___b___b___b___EXON 3 (ALPHA 2 DOMAIN)_b___b___b___b___b___>

490       500       510       520
     .         .         .         .
ACG GCG GCG GAC ATG GCG GCG CAG ATC ACC CGA CGC AAG TGG GAG CAG
Thr Ala Ala Asp Met Ala Ala Gln Ile Thr Arg Arg Lys Trp Glu Gln>
___b___b___b___b___EXON 3 (ALPHA 2 DOMAIN)_b___b___b___b___b___>

530       540       550       560       570
 .         .         .         .         .
GCT GGT GCT GCA GAG AGA GAC CGG GCC TAC CTG GAG GGC GAG TGC GTG
Ala Gly Ala Ala Glu Arg Asp Arg Ala Tyr Leu Glu Gly Glu Cys Val>
___b___b___b___b___EXON 3 (ALPHA 2 DOMAIN)_b___b___b___b___b___>

580       590       600       610       620
     .         .         .         .         .
GAG TGG CTC CGC AGA TAC CTG AAG AAC GGG AAT GCT ACG CTG CTG CGC
Glu Trp Leu Arg Arg Tyr Leu Lys Asn Gly Asn Ala Thr Leu Leu Arg>
```

Sequence ID No:1. A nucleic acid encoding the D$^d$ MHC.

```
___b___b___b___b___EXON 3 (ALPHA 2 DOMAIN)_b___b___b___b___b___>
       630         640         650         660         670
        .           .           .           .           .
ACA GAT CCC CCA AAG GCC CAT GTG ACC CAT CAC CGC AGA CCT GAA GGT
Thr Asp Pro Pro Lys Ala His Val Thr His His Arg Arg Pro Glu Gly>
___>
       ___c___c___c___c_EXON 4 (ALPHA 3 DOMAIN)___c___c___c___c___>
       680         690         700         710         720
        .           .           .           .           .
GAT GTC ACC CTG AGG TGC TGG GCC CTG GGC TTC TAC CCT GCT GAC ATC
Asp Val Thr Leu Arg Cys Trp Ala Leu Gly Phe Tyr Pro Ala Asp Ile>
___c___c___c___c___EXON 4 (ALPHA 3 DOMAIN)_c___c___c___c___c___>
           730         740         750         760
            .           .           .           .
ACC CTG ACC TGG CAG TTG AAT GGG GAG GAG CTG ACC CAG GAA ATG GAG
Thr Leu Thr Trp Gln Leu Asn Gly Glu Glu Leu Thr Gln Glu Met Glu>
___c___c___c___c___EXON 4 (ALPHA 3 DOMAIN)_c___c___c___c___c___>
770         780         790         800         810
 .           .           .           .           .
CTT GTG GAG ACC AGG CCT GCA GGG GAT GGA ACC TTC CAG AAG TGG GCA
Leu Val Glu Thr Arg Pro Ala Gly Asp Gly Thr Phe Gln Lys Trp Ala>
___c___c___c___c___EXON 4 (ALPHA 3 DOMAIN)_c___c___c___c___c___>
       820         830         840         850         860
        .           .           .           .           .
TCT GTG GTG GTG CCT CTT GGG AAG GAG CAG AAG TAC ACA TGC CAT GTG
Ser Val Val Val Pro Leu Gly Lys Glu Gln Lys Tyr Thr Cys His Val>
___c___c___c___c___EXON 4 (ALPHA 3 DOMAIN)_c___c___c___c___c___>
       870         880         890         900         910
        .           .           .           .           .
GAA CAT GAG GGG CTG CCT GAG CCC CTC ACC CTG AGA TGG GGC AAG GAG
Glu His Glu Gly Leu Pro Glu Pro Leu Thr Leu Arg Trp Gly Lys Glu>
___c___c___c___c___EXON 4 (ALPHA 3 DOMAIN)_c___c___c___c___c___>
       920         930         940         950         960
        .           .           .           .           .
GAG CCT CCT TCA TCC ACC AAG ACT AAC ACA GTA ATC ATT GCT GTT CCG
Glu Pro Pro Ser Ser Thr Lys Thr Asn Thr Val Ile Ile Ala Val Pro>
___d___d___d___d___EXON 5 (TRANSMEMBRANE)_d___d___d___d___d___>
           970         980         990         1000
            .           .           .           .
GTT GTC CTT GGA GCT GTG GTC ATC CTT GGA GCT GTG ATG GCT TTT GTG
Val Val Leu Gly Ala Val Val Ile Leu Gly Ala Val Met Ala Phe Val
___d___d___d___d___EXON 5 (TRANSMEMBRANE)_d___d___d___d___d___>
1010        1020        1030        1040        1050
 .           .           .           .           .
ATG AAG AGG AGG AGA AAC ACA GGT GGA AAA GGA GGG GAC TAT GCT CTG
Met Lys Arg Arg Arg Asn Thr Gly Gly Lys Gly Gly Asp Tyr Ala Leu>
___EXON 5 (TRANSMEMBRAN____>
                       ___e__EXON 6 (TRANSMEMBRANE)___e___>
1060        1070        1080        1090        1100
 .           .           .           .           .
GCT CCA GGC TCC CAG AGC TCT GAT ATG TCT CTC CCA GAT TGT AAA GTG
Ala Pro Gly Ser Gln Ser Ser Asp Met Ser Leu Pro Asp Cys Lys Val>
___e___>
       ___f___f___f___f___f__EXON 7___f___f___f___f___f___>
                                                        ___>
       1110        1120        1130        1140        1150
        .           .           .           .           .
TGA AGA CAG CTG CCT AGT GTG GAC TTG GTG ACA GAC AAT GTC TTC AGA
...>
___>
           1160        1170        1180
            .           .           .
CAT CTC CTG TGA CAT CCA GAG ACC TGA ATT C
```

What is claimed is:

1. A recombinant nucleic acid molecule encoding a fusion protein, wherein the fusion protein comprises an extracellular domain, a transmembrane domain, and an intracellular domain,
wherein the extracellular domain comprises an α or β chain extracellular domain of a Class II AMC polypeptide or an extracellular domain of a class I MHC polypeptide, and
wherein the intracellular domain comprises a T cell receptor zeta chain polypeptide intracellular domain.

2. The recombinant nucleic acid molecule of claim 1, wherein the extracellular domain of the Class I MHC polypeptide comprises an extracellular domain of a human HLA heavy chain polypeptide.

3. The recombinant nucleic acid molecule of claim 1, wherein the transmembrane domain comprises a T cell receptor zeta chain transmembrane domain.

4. The recombinant nucleic acid molecule of claim 1, wherein the transmembrane domain comprises a Class I HLA transmembrane domain.

5. The recombinant nucleic acid molecule of claim 1, wherein the transmembrane domain is a hybrid domain comprising sequences from both a T cell receptor zeta chain transmembrane domain and a Class I HLA transmembrane domain.

6. An expression vector comprising a nucleic acid encoding a fusion protein, wherein the fusion protein comprises an extracellular domain, a transmembrane domain, and an intracellular domain,
wherein the extracellular domain comprises an α or β chain extracellular domain of a Class II MHC polypeptide or an extracellular domain of a class I MHC polypeptide, and
wherein the intracellular domain comprises a T cell receptor zeta chain polypeptide intracellular domain and wherein the fusion protein encoding nucleic acid is operably linked to a promoter.

7. The expression vector of claim 6, wherein the fusion protein-encoding nucleic acid is operably linked to a T cell specific promoter.

8. The expression vector of claim 7, wherein the T cell specific promoter is a CD2 promoter, a Lck promoter, a CD3 promoter or a CD4 promoter.

9. A transfected cell comprising a recombinant nucleic acid molecule encoding a fusion protein, wherein the fusion protein comprises an extracellular domain, a transmembrane domain, and an intracellular domain,
wherein the extracellular domain comprises an α or β chain extracellular domain of a Class II MHC polypeptide or an extracellular domain of a class I MHC polypeptide, and
wherein the intracellular domain comprises a T cell receptor zeta chain polypeptide intracellular domain and wherein said transfected cell expresses said fusion protein.

10. The transfected cell of claim 9, wherein the cell is a T cell.

11. The transfected cell of claim 9, wherein the T cell is a cytotoxic T cell, a helper T cell, or a hematopoietic stem cell.

12. The transfected cell of claim 9, wherein the cell is a human cell.

13. A pharmaceutical composition comprising a transfected cell suspended in a pharmaceutically acceptable aqueous carrier, wherein the transfected cell comprises a recombinant nucleic acid molecule encoding a fusion protein, wherein the fusion protein comprises an extracellular domain, a transmembrane domain, and an intracellular domain, wherein the extracellular domain comprises an extracellular domain of a Class I MHC polypeptide wherein the intracellular domain comprises a T cell receptor zeta chain polypeptide intracellular domain and wherein said transfected cell expresses said fusion protein.

14. A method of delaying T cell mediated rejection of a tissue, cell graft or organ transplant in a recipient of the graft or transplant, wherein the graft or transplant expresses a Class I major histocompatibility antigen not expressed by the recipient, comprising: administering a pharmaceutical composition comprising transfected T lymphocytes or hematopoietic stem cells suspended in a pharmaceutically acceptable aqueous carrier in an amount sufficient to delay T cell mediated rejection of the tissue, cell graft or organ transplant, wherein the transfected cell comprises a recombinant nucleic acid molecule encoding a fusion protein, wherein the fusion protein comprises an MHC class I extracellular domain, a transmembrane domain, and a T cell receptor zeta chain polypeptide intracellular domain, wherein the MHC Class I antigen is expressed by the tissue, cell graft, or organ transplant and is not expressed by the recipient, and wherein the expression of said fusion protein results in a delay in T cell mediated graft rejection of said tissue, cell graft or organ transplant.

15. The method of claim 14, wherein the T lymphocyte is a cytotoxic T cell or a helper T cell.

16. The method of claim 14, wherein the tissue graft is a skin graft.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

TAAATTCTCG AGGGATCCCA GATGGGGGCG                             30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CTGCACGAAT TCTCTCCTCC TCCTCATCAC                             30

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TCGTATGAAT TCGCAAAATT CAGCAGGAGT GCAGAG                      36

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CTAGCTAGAT CTAAGCTTGC ATGCCTGCAG GTCGAC                      36

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
TCAAGCTTGC ATGCCTGC                                                    18

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATCCTCCTTG CCCCATCTC                                                   19

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GATCCCAAAC TCTGCTACTT GCTAGAT                                          27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TGATCTAGAA ATGCCCTGGC TGTTAGC                                          27

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GGAGGAGGCA GGTGACTA                                                    18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

ATCCCATCTC AGGGTGAG                                                    18
```

(2) INFORMATION FOR SEQ ID NO:11:

(i) SEQUENCE CHARACTERISTICS:
        (A) LENGTH: 1183 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 82..1107
        (D) OTHER INFORMATION: /product= "d-D MHC"
            /note= "nucleic acid encoding d-D MHC"

(xi) SEQUENCE DESCRIPTION: SEQ ID NO:11:

```
GGATCCCAGA TGGGGGCGAT GGCTCCGCGC ACGCTGCTCC TGCTGCTGGC GGCCGCCCTG           60

GGTCCGACTC AGACCCGCGC T GGC TCA CAC TCG CTG AGG TAT TTC GTC ACC           111
                        Gly Ser His Ser Leu Arg Tyr Phe Val Thr
                          1               5                  10

GCC GTG TCC CGG CCC GGC TTC GGG GAG CCC CGG TAC ATG GAA GTC GGC           159
Ala Val Ser Arg Pro Gly Phe Gly Glu Pro Arg Tyr Met Glu Val Gly
                 15                  20                  25

TAC GTG GAC AAC ACG GAG TTC GTG CGC TTC GAC AGC GAC GCG GAG AAT           207
Tyr Val Asp Asn Thr Glu Phe Val Arg Phe Asp Ser Asp Ala Glu Asn
             30                  35                  40

CCG AGA TAT GAG CCG CGG GCG CGG TGG ATA GAG CAG GAG GGG CCG GAG           255
Pro Arg Tyr Glu Pro Arg Ala Arg Trp Ile Glu Gln Glu Gly Pro Glu
         45                  50                  55

TAT TGG GAG CGG GAG ACA CGG AGA GCC AAG GGC AAT GAG CAG AGT TTC           303
Tyr Trp Glu Arg Glu Thr Arg Arg Ala Lys Gly Asn Glu Gln Ser Phe
     60                  65                  70

CGA GTG GAC CTG AGG ACC GCG CTG CGC TAC TAC AAC CAG AGC GCG GGC           351
Arg Val Asp Leu Arg Thr Ala Leu Arg Tyr Tyr Asn Gln Ser Ala Gly
 75                  80                  85                  90

GGC TCT CAC ACA CTC CAG TGG ATG GCT GGC TGT GAC GTG GAG TCG GAC           399
Gly Ser His Thr Leu Gln Trp Met Ala Gly Cys Asp Val Glu Ser Asp
                 95                 100                 105

GGG CGC CTC CTC CGC GGG TAC TGG CAG TTC GCC TAC GAC GGC TGC GAT           447
Gly Arg Leu Leu Arg Gly Tyr Trp Gln Phe Ala Tyr Asp Gly Cys Asp
            110                 115                 120

TAC ATC GCC CTG AAC GAA GAC CTG AAA ACG TGG ACG GCG GCG GAC ATG           495
Tyr Ile Ala Leu Asn Glu Asp Leu Lys Thr Trp Thr Ala Ala Asp Met
        125                 130                 135

GCG GCG CAG ATC ACC CGA CGC AAG TGG GAG CAG GCT GGT GCT GCA GAG           543
Ala Ala Gln Ile Thr Arg Arg Lys Trp Glu Gln Ala Gly Ala Ala Glu
    140                 145                 150

AGA GAC CGG GCC TAC CTG GAG GGC GAG TGC GTG GAG TGG CTC CGC AGA           591
Arg Asp Arg Ala Tyr Leu Glu Gly Glu Cys Val Glu Trp Leu Arg Arg
155                 160                 165                 170

TAC CTG AAG AAC GGG AAT GCT ACG CTG CTG CGC ACA GAT CCC CCA AAG           639
Tyr Leu Lys Asn Gly Asn Ala Thr Leu Leu Arg Thr Asp Pro Pro Lys
                175                 180                 185

GCC CAT GTG ACC CAT CAC CGC AGA CCT GAA GGT GAT GTC ACC CTG AGG           687
Ala His Val Thr His His Arg Arg Pro Glu Gly Asp Val Thr Leu Arg
            190                 195                 200

TGC TGG GCC CTG GGC TTC TAC CCT GCT GAC ATC ACC CTG ACC TGG CAG           735
Cys Trp Ala Leu Gly Phe Tyr Pro Ala Asp Ile Thr Leu Thr Trp Gln
        205                 210                 215

TTG AAT GGG GAG GAG CTG ACC CAG GAA ATG GAG CTT GTG GAG ACC AGG           783
Leu Asn Gly Glu Glu Leu Thr Gln Glu Met Glu Leu Val Glu Thr Arg
    220                 225                 230
```

-continued

```
CCT GCA GGG GAT GGA ACC TTC CAG AAG TGG GCA TCT GTG GTG GTG CCT      831
Pro Ala Gly Asp Gly Thr Phe Gln Lys Trp Ala Ser Val Val Val Pro
235                 240                 245                 250

CTT GGG AAG GAG CAG AAG TAC ACA TGC CAT GTG GAA CAT GAG GGG CTG      879
Leu Gly Lys Glu Gln Lys Tyr Thr Cys His Val Glu His Glu Gly Leu
                255                 260                 265

CCT GAG CCC CTC ACC CTG AGA TGG GGC AAG GAG GAG CCT CCT TCA TCC      927
Pro Glu Pro Leu Thr Leu Arg Trp Gly Lys Glu Glu Pro Pro Ser Ser
            270                 275                 280

ACC AAG ACT AAC ACA GTA ATC ATT GCT GTT CCG GTT GTC CTT GGA GCT      975
Thr Lys Thr Asn Thr Val Ile Ile Ala Val Pro Val Val Leu Gly Ala
        285                 290                 295

GTG GTC ATC CTT GGA GCT GTG ATG GCT TTT GTG ATG AAG AGG AGG AGA     1023
Val Val Ile Leu Gly Ala Val Met Ala Phe Val Met Lys Arg Arg Arg
    300                 305                 310

AAC ACA GGT GGA AAA GGA GGG GAC TAT GCT CTG GCT CCA GGC TCC CAG     1071
Asn Thr Gly Gly Lys Gly Gly Asp Tyr Ala Leu Ala Pro Gly Ser Gln
315                 320                 325                 330

AGC TCT GAT ATG TCT CTC CCA GAT TGT AAA GTG TGAAGACAGC TGCCTAGTGT   1124
Ser Ser Asp Met Ser Leu Pro Asp Cys Lys Val
                335                 340

GGACTTGGTG ACAGACAATG TCTTCACACA TCTCCTGTGA CATCCAGAGA CCTGAATTC    1183
```

(2) INFORMATION FOR SEQ ID NO:12:

(i) SEQUENCE CHARACTERISTICS:
      (A) LENGTH: 341 amino acids
      (B) TYPE: amino acid
      (D) TOPOLOGY: linear (ii) MOLECULE TYPE: protein (xi) SEQUENCE DESCRIPTION: SEQ ID NO:12:

```
Gly Ser His Ser Leu Arg Tyr Phe Val Thr Ala Val Ser Arg Pro Gly
 1               5                  10                  15

Phe Gly Glu Pro Arg Tyr Met Glu Val Gly Tyr Val Asp Asn Thr Glu
             20                  25                  30

Phe Val Arg Phe Asp Ser Asp Ala Glu Asn Pro Arg Tyr Glu Pro Arg
         35                  40                  45

Ala Arg Trp Ile Glu Gln Glu Gly Pro Glu Tyr Trp Glu Arg Glu Thr
     50                  55                  60

Arg Arg Ala Lys Gly Asn Glu Gln Ser Phe Arg Val Asp Leu Arg Thr
 65                  70                  75                  80

Ala Leu Arg Tyr Tyr Asn Gln Ser Ala Gly Gly Ser His Thr Leu Gln
                 85                  90                  95

Trp Met Ala Gly Cys Asp Val Glu Ser Asp Gly Arg Leu Leu Arg Gly
            100                 105                 110

Tyr Trp Gln Phe Ala Tyr Asp Gly Cys Asp Tyr Ile Ala Leu Asn Glu
        115                 120                 125

Asp Leu Lys Thr Trp Thr Ala Ala Asp Met Ala Ala Gln Ile Thr Arg
    130                 135                 140

Arg Lys Trp Glu Gln Ala Gly Ala Ala Glu Arg Asp Arg Ala Tyr Leu
145                 150                 155                 160

Glu Gly Glu Cys Val Glu Trp Leu Arg Arg Tyr Leu Lys Asn Gly Asn
                165                 170                 175

Ala Thr Leu Leu Arg Thr Asp Pro Pro Lys Ala His Val Thr His His
            180                 185                 190
```

-continued

```
Arg Arg Pro Glu Gly Asp Val Thr Leu Arg Cys Trp Ala Leu Gly Phe
        195                 200                 205

Tyr Pro Ala Asp Ile Thr Leu Thr Trp Gln Leu Asn Gly Glu Glu Leu
    210                 215                 220

Thr Gln Glu Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Lys
                245                 250                 255

Tyr Thr Cys His Val Glu His Glu Gly Leu Pro Glu Pro Leu Thr Leu
            260                 265                 270

Arg Trp Gly Lys Glu Glu Pro Pro Ser Ser Thr Lys Thr Asn Thr Val
        275                 280                 285

Ile Ile Ala Val Pro Val Val Leu Gly Ala Val Val Ile Leu Gly Ala
    290                 295                 300

Val Met Ala Phe Val Met Lys Arg Arg Arg Asn Thr Gly Gly Lys Gly
305                 310                 315                 320

Gly Asp Tyr Ala Leu Ala Pro Gly Ser Gln Ser Ser Asp Met Ser Leu
                325                 330                 335

Pro Asp Cys Lys Val
            340

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Tyr Xaa Xaa Leu
```